United States Patent
Lyke et al.

(10) Patent No.: US 10,950,139 B1
(45) Date of Patent: Mar. 16, 2021

(54) METHODS AND APPARATUS FOR COACHING BASED ON WORKOUT HISTORY AND READINESS/RECOVERY INFORMATION

(71) Applicant: Under Armour, Inc., Baltimore, MD (US)

(72) Inventors: James Lyke, Austin, TX (US); Ben Hamill, Austin, TX (US); Jeff Knight, Austin, TX (US); Scott Laing, Austin, TX (US)

(73) Assignee: MyFitnessPal, Inc., San Francisco, CA (US)

( * ) Notice: Subject to any disclaimer, the term of this patent is extended or adjusted under 35 U.S.C. 154(b) by 0 days.

(21) Appl. No.: 16/721,149

(22) Filed: Dec. 19, 2019

Related U.S. Application Data

(63) Continuation-in-part of application No. 16/588,199, filed on Sep. 30, 2019.

(51) Int. Cl.
| | |
|---|---|
| *G16H 20/30* | (2018.01) |
| *G09B 5/00* | (2006.01) |
| *G09B 19/00* | (2006.01) |
| *G09B 5/04* | (2006.01) |
| *G09B 5/02* | (2006.01) |

(52) U.S. Cl.
CPC ............... *G09B 19/00* (2013.01); *G09B 5/00* (2013.01); *G16H 20/30* (2018.01); *G09B 5/02* (2013.01); *G09B 5/04* (2013.01)

(58) Field of Classification Search
CPC ... G09B 5/00; G09B 5/02; G09B 5/04; G16H 20/30
See application file for complete search history.

(56) References Cited

U.S. PATENT DOCUMENTS

| | | | | |
|---|---|---|---|---|
| 9,691,023 | B2 * | 6/2017 | Barnes | G09B 7/02 |
| 10,065,074 | B1 * | 9/2018 | Hoang | G16H 40/63 |
| 2005/0113650 | A1 * | 5/2005 | Pacione | A61B 5/4809 |
| | | | | 600/300 |
| 2008/0214905 | A1 * | 9/2008 | Francescato | A61B 5/72 |
| | | | | 600/301 |
| 2009/0069156 | A1 * | 3/2009 | Kurunmaki | A63B 24/0062 |
| | | | | 482/9 |
| 2015/0251074 | A1 * | 9/2015 | Ahmed | G06F 1/3206 |
| | | | | 700/91 |
| 2017/0329933 | A1 * | 11/2017 | Brust | G06F 16/252 |

* cited by examiner

*Primary Examiner* — Robert J Utama
(74) *Attorney, Agent, or Firm* — Law Office of Mark Wang, P.C.

(57) ABSTRACT

System and method for coaching based on workout history and/or readiness/recovery information. Improved solutions enable intelligent management of a user's personal fitness journey based on workout recommendations that closely align with the user's traits. In one exemplary embodiment, workout data for a population of different individuals is analyzed to identify groups of similarly performing individuals. Each group of individuals is analyzed to generate an expected profile that approximates the physiological and/or psychological traits of the group. An expected profile includes heuristics and/or performance metrics that enable dynamic coaching during workouts. Subsequently thereafter, users can be dynamically coached by their client device, based on the expected profile.

20 Claims, 15 Drawing Sheets

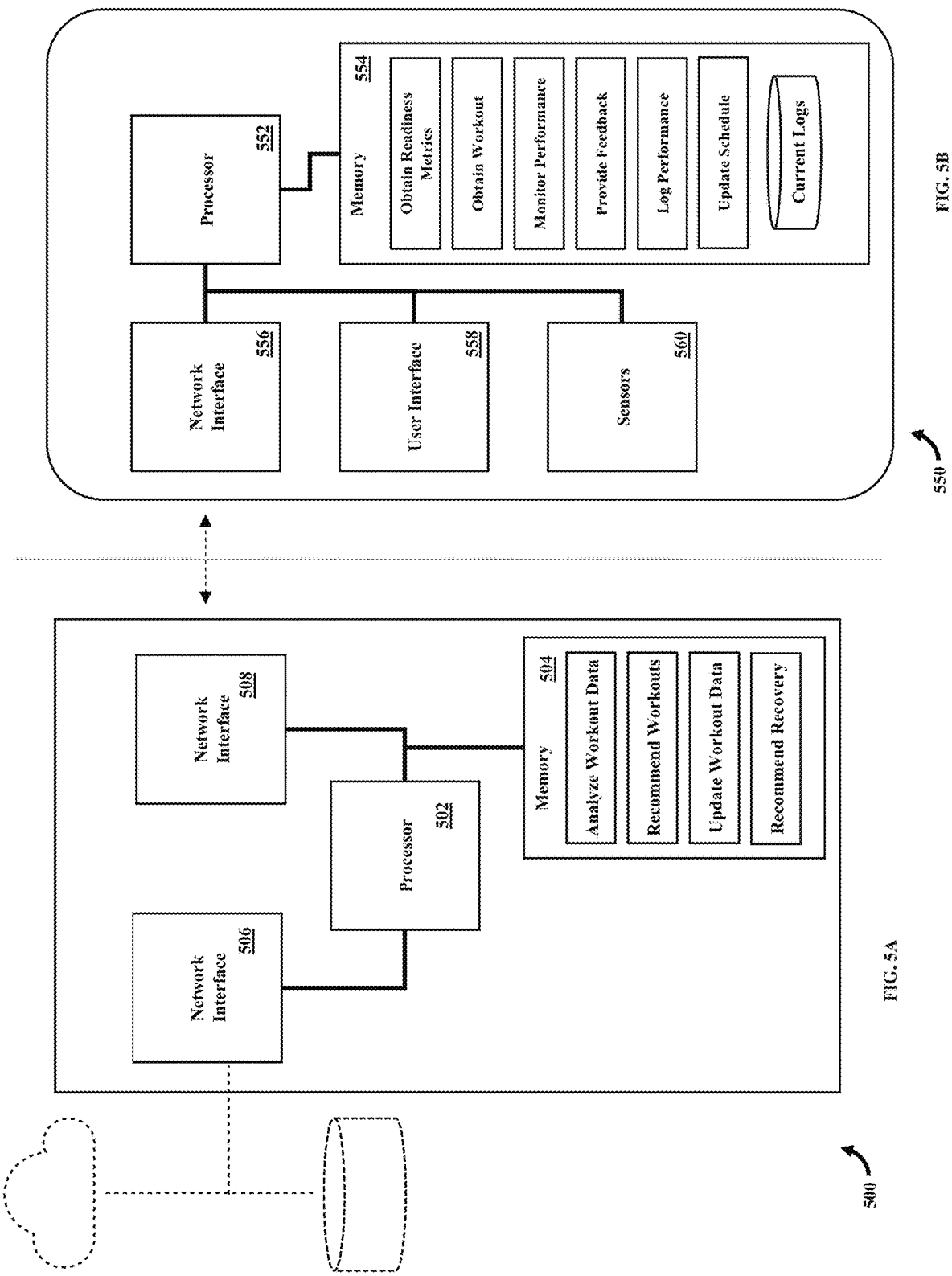

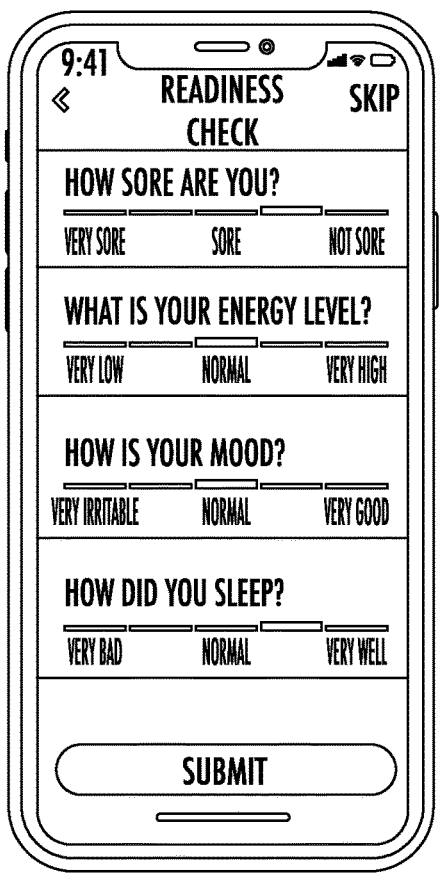 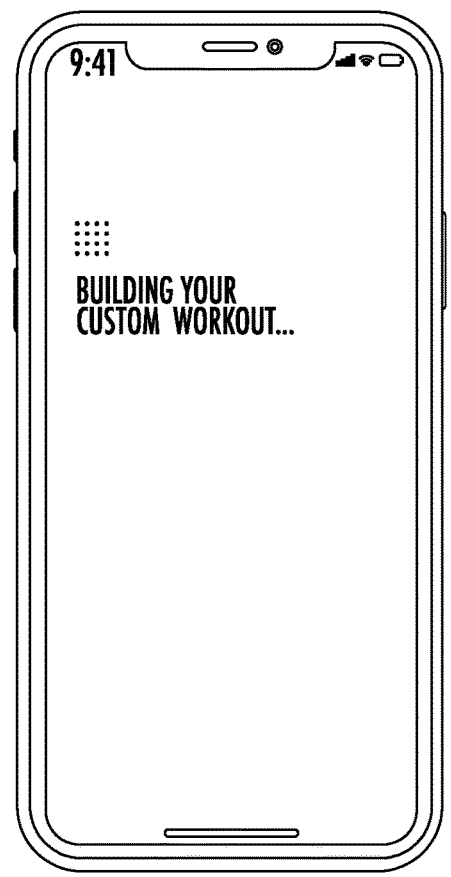
PRE WKO READINESS — DYNAMIC UPDATE
FIG. 6D

METHODS AND APPARATUS FOR COACHING BASED ON WORKOUT HISTORY AND READINESS/RECOVERY INFORMATION

PRIORITY

This application is a continuation-in-part and claims the benefit of priority to co-owned and co-pending U.S. patent application Ser. No. 16/588,199, entitled "METHODS AND APPARATUS FOR COACHING BASED ON WORKOUT HISTORY", filed Sep. 30, 2019, the contents of which are incorporated herein by reference in their entireties.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

TECHNICAL FIELD

This disclosure relates generally to the field of personal fitness. More particularly, the present disclosure relates to systems, computer programs, devices, and methods for coaching a user.

DESCRIPTION OF RELATED TECHNOLOGY

In recent years, health and fitness tracking applications that track user workouts and activities have become very popular. Routine physical activity is important to a healthy lifestyle and is known to prevent and/or ameliorate various health conditions, such as diabetes and obesity. Health and fitness tracking applications allow users to set and achieve personalized health goals by tracking the amount of physical activity, regularity of physical activity, and/or intensity of physical activity. These applications enable users to gain insights regarding their workout regimen efficacy.

However, existing health and fitness tracking applications often suggest workout routines based on generalizations of the human body and/or assumptions about workout performance. Hence what is needed are improved methods for providing workout recommendations and coaching.

SUMMARY

The present disclosure addresses the foregoing needs by disclosing, inter alia, methods, devices, systems, and computer programs for coaching a user based on workout history, readiness/recovery information, and/or personal fitness goals, thereby providing improved workout recommendations and coaching.

In one aspect, a method for dynamically coaching a user based on one or more readiness metrics is disclosed. In one embodiment, the method includes: monitoring the one or more readiness metrics; obtaining a recommended workout and a profile, the profile comprising a performance metric; adjusting the performance metric based on the one or more readiness metrics; monitoring a performance during the recommended workout; and when the performance does not match the adjusted performance metric, providing dynamic feedback.

In one variant, the one or more readiness metrics comprises an amount or quality of sleep.

In one variant, the one or more readiness metrics comprises an estimated caloric availability.

In one variant, the one or more readiness metrics comprises a subjective input provided by the user.

In one variant, the method further includes adjusting the recommended workout based on a start time, an end time, or a shortened available duration.

In one variant, the dynamic feedback is additionally based on the one or more readiness metrics.

In one variant, the method further includes updating a workout data record based on the one or more readiness metrics.

In one aspect, a method for providing a user with recovery coaching is disclosed. In one embodiment, the method includes: obtaining a recommended workout and a profile comprising a performance metric; monitoring a performance during the recommended workout; when the performance does not match the performance metric, providing dynamic feedback; and updating a schedule based on the performance.

In one variant, the schedule includes a suggested rest event or a suggested post-workout consumption event.

In one variant, the updating includes modifying the suggested rest event, wherein the modified suggested rest event is based on the performance.

In one variant, the updating includes modifying the suggested post-workout consumption event, wherein the modified suggested post-workout consumption event is based on the performance.

In one variant, the updating includes adding a suggested rest event or a suggested post-workout consumption event. In one such variant, the method further includes creating a data record based on a completion status of the suggested rest event or the suggested post-workout consumption event. In one such variant, the updating the profile is based on at least the data record.

In one aspect, a user apparatus is disclosed. In one embodiment, the user apparatus includes: a user interface; a network interface; a processor; and a non-transitory computer-readable medium. In one exemplary embodiment, the non-transitory computer-readable medium includes one or more instructions, which when executed by the processor, causes the user apparatus to: collect at least one of a readiness metric or a recovery metric; obtain a recommended workout and a profile comprising a performance metric; and monitor performance during the recommended workout.

In one variant, the user apparatus includes a sleep tracking sensor and the readiness metric includes an amount or quality of sleep measured before the recommended workout.

In one variant, the user apparatus includes a sleep tracking sensor and the recovery metric includes an actual amount or quality of sleep measured after the recommended workout.

In one variant, the one or more instructions, when executed by the processor, further cause the user apparatus to: log one or more consumption events; and estimate the readiness metric based on the one or more consumption events before the recommended workout.

In one variant, the one or more instructions, when executed by the processor, further cause the user apparatus to: log one or more consumption events; and estimate the recovery metric based on the one or more consumption events after the recommended workout.

In one variant, the one or more instructions, when executed by the processor, further cause the user apparatus to: solicit subjective user input prior to the recommended workout; and estimate the readiness metric based on the subjective user input.

More generally, various aspects of the present disclosure are directed to systems, apparatus, methods and storage media that coach a user based on workout history, readiness/recovery information, and/or personal fitness goals.

Other features and advantages of the present disclosure will immediately be recognized by persons of ordinary skill in the art with reference to the attached drawings and detailed description of exemplary embodiments as given below.

BRIEF DESCRIPTION OF THE DRAWINGS

FIGS. 5A-5B are logical block diagrams of an exemplary server apparatus and health tracking devices useful in conjunction therewith, in accordance with the various principles described herein.

FIGS. 6A-6F are graphical representations of one exemplary user interface, consistent with the various principles described herein.

Figure 1:
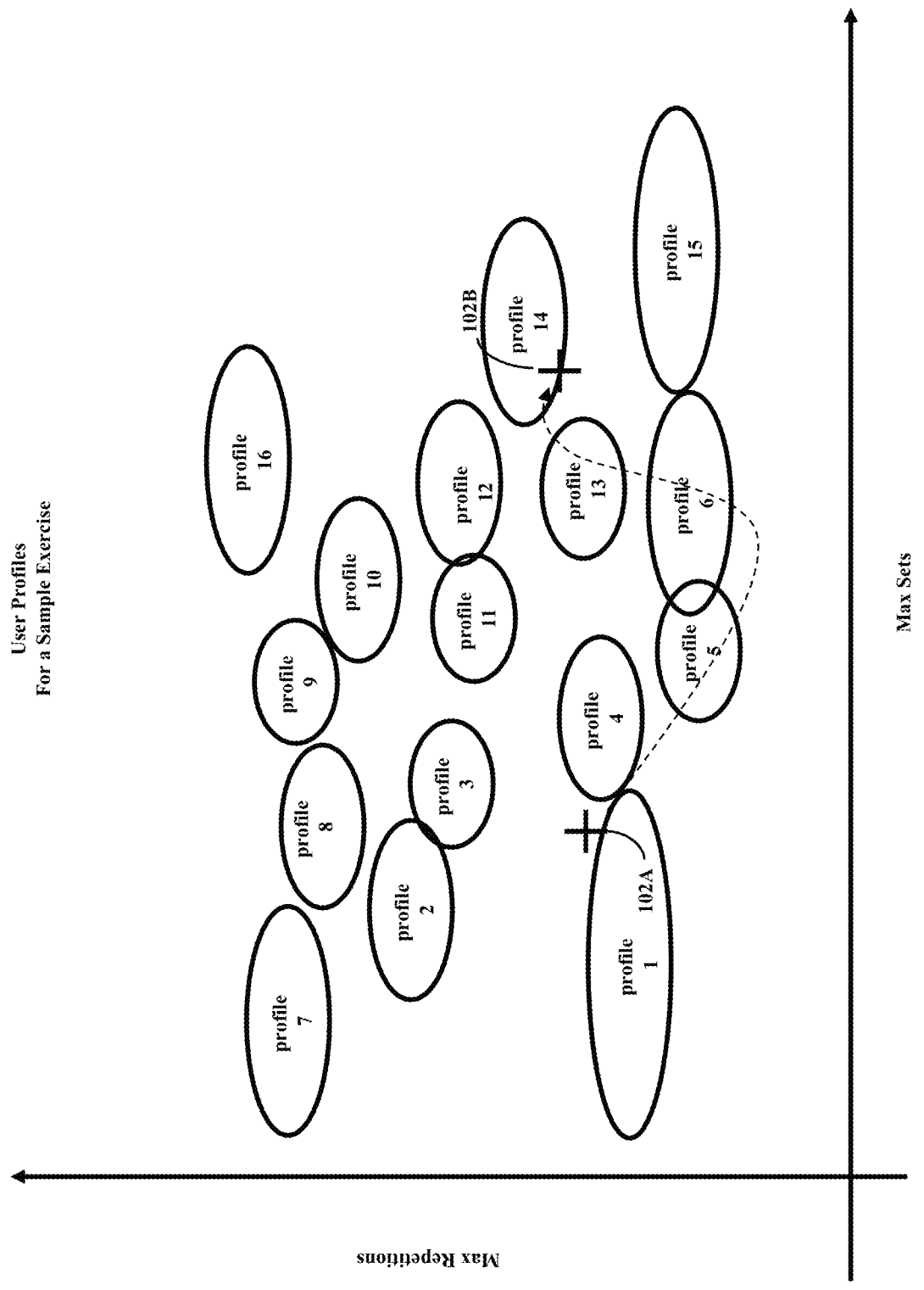
FIG. 1 is a graphical representation of user assessment, in accordance with the various principles described herein.

All Figures © Under Armour, Inc. 2019. Rights Reserved

DETAILED DESCRIPTION

Disclosed embodiments include systems, apparatus, methods and storage media which enable workout recommendations and coaching based on workout history, readiness/recovery information, and/or personal fitness goals.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without departing from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

Workout Routines, Rest and Recovery, and Human Physiology and Psychology

Most holistic health and fitness goals include some aspect of strength training and cardiovascular exercise. Similarly, many athletic activities (recreational, amateur, and/or professional) require significant strength and cardiovascular exertion. Thus, workout routines are generally categorized into cardiovascular workouts (e.g., walking, running, swimming, biking, etc.) and strength workouts (e.g., weightlifting, sprints, etc.) Some hybridized workout regimens mix both cardiovascular and strength training.

As a brief aside, the human body's cardiovascular system circulates oxygen and removes waste products from the skeletal muscles by pumping blood. The cardiovascular system relies on a unique type of cardiac muscle fiber to accomplish this task; cardiac muscle fiber is an involuntarily controlled muscle that is highly specialized and found nowhere else in the human body. The cardiovascular system's performance remains remarkably consistent over prolonged exertion.

In contrast to cardiac muscles, skeletal muscles are part of the human skeletal system (e.g., muscles, bones, tendons, ligaments, etc.) Skeletal muscles fatigue as a function of duration and intensity of use; their performance can be highly dynamic depending on composition. Modern research has shown that skeletal muscles are 3-dimensional structures of varying muscle fibers and connective tissue. Human muscle fibers are generally classified as "slow twitch" and "fast twitch", however muscle fiber types exist on a continuum and can express both slow and fast twitch qualities. The structure of skeletal muscles widely varies among different people; for example, some people may have muscle compositions that can easily provide bursts of activity at high load, others may have muscle compositions that provide sustained endurance at lower loads, etc.

Humans widely vary in their baseline physiology and psychology; these differences affect workout efficacy; for example, two people of different height, weight, fitness, musculature, and mental outlook may run 5 miles or lift weights with different levels of exertion and performance progression. As a practical matter, individual differences can introduce problems for people that exercise with a particular goal in mind.

For instance, most strength training routines are static and/or inflexible e.g., "20 kettle bell swings, 15 pounds", "15 bicep curls at 80% of maximum." Similarly, since the cardiovascular system is involuntary, cardiovascular workouts only indirectly exercise the muscles based on physical activity. Most endurance workouts prescribe a set time, set distance, etc. (e.g., "run 5 miles", "bike for 30 minutes.") Typically, these static workout routines assume a particular musculature and/or fitness level; there is no way to dynamically adjust the workout routine to suit individual needs. For example, a person that has suffered an injury may need to change a workout routine to prevent further injury. In another such example, a person may select a workout for 45 minutes during a lunch break but end up finishing too early (or take too long). In yet another example, a person may not be able to use required equipment (e.g., a specialized machine may be too busy during certain gym hours.) Even if the person has completed a modified workout, they may incorrectly log the workout data in their health and fitness tracking applications (e.g., over/under report activity, etc.)

As but another example, athletes often tailor their workout regime so as to improve performance for a particular athletic motion (e.g., throwing a ball, etc.) Many athletic activities incorporate multiple muscle groups working in concert (e.g., throwing a ball requires the arms, chest, back, stomach, and leg muscles to fluidly coordinate.) In contrast, most workout techniques and weightlifting equipment are focused on a single (or few) muscle group(s). While a professional athlete may be closely scrutinized by physical therapists and prescribed specific muscle group workouts to tune their performance, amateur and/or casual hobbyists seldom have access to the same resources. Instead they may resort to imperfectly copying workouts for lack of better alternatives. Unfortunately, this may result in widely diverging performance gains merely because they've over/under emphasized certain muscle groups.

As a related note, individual behaviors and motivations span a wide range. Some individuals are highly goal oriented in their workout regimen; other individuals may enjoy working out to "blow off steam." Some individuals may work through pain, even to their own detriment; others may need encouragement when a workout is difficult (but still doable). As a practical matter, these "intangible" factors are impossible to capture in static workout recommendations. Currently, dynamic feedback is only possible in the form of a human personal trainer/coach that actively observes an individual's workout; unfortunately, hiring a personal trainer can be cost-prohibitive for most gym goers.

Certain companies and/or gyms regularly publish workout routines via e.g., applications and websites, blogs, and other media sources, to boost gym attendance and/or attract new subscribers. While these services may provide well-intentioned information and/or generally acceptable guidance, there are no cost-effective solutions that are individually tailored. Furthermore, individuals with specific goals may be well aware of their own limitations and/or idiosyncrasies, and yet be unable to find workout routines that are germane to their personal fitness journey.

As but another complication, while common sense and empirical evidence suggests that sleep and nutrition are important for pre-workout readiness and post-workout recovery, most workout regimens are focused on the workout itself (e.g., sets, reps, heart rate, etc.) The interplay between sleep, nutrition, and workout performance is largely unresearched and/or poorly characterized.

Notably, existing sleep and/or nutrition tracking is primarily focused on long term behaviors and effects. For example, sleep tracking has been used in medical treatment for chronic sleeping issues (e.g., insomnia, oversleeping, etc.). Even though many health tracking devices can monitor a user's sleep on a day-to-day basis, existing devices do not address the user-specific short term (e.g., next day) effects of sleep deprivation on performance.

Similarly, most consumers use meal tracking for weight loss. However, weight loss is a gradual process that takes weeks (if not months or even years) to see consistent results. Existing meal tracking applications do not address the immediate effects of consumption; e.g., meal tracking applications do not plan meals around user-specific blood sugar metabolism and/or caloric requirements for upcoming activities.

Non-workout behaviors may greatly impact the user's instantaneous workout "readiness" and/or "recovery". Unfortunately, as with other physiological and/or psychological aspects, humans widely vary in their required sleep and/or nutrition. For example, even though a poorly rested user is likely to be undermotivated and underperform; "poor rest" can widely vary across the population (e.g., 7 hours of sleep may be too much for one user, but more than enough for another). Similarly, failing to refuel with adequate macronutrients (e.g., protein, carbohydrates and/or fats) can result in suboptimal muscle recovery. However, different people metabolize food at different rates; a protein shake may work for one user but be wholly inadequate for another. More directly, existing sleep and nutrition techniques are poorly suited for dynamic workout coaching.

In view of the existing health and fitness ecosystem, improved solutions are needed to enable consumers to intelligently navigate their personal fitness journey. There exists a persistent need to provide efficient and easy-to-use mechanisms for getting relevant workout recommendations and coaching.

Example Operation

The exemplary solution described herein addresses the foregoing by providing workout routine coaching based on e.g., workout history, readiness/recovery information, and/or personal fitness goals. As previously alluded to, the wide variation in human physiology and psychology cannot be adequately addressed by static workout routines, one-size-fits all readiness and recovery guidance, and fixed workout progressions. However, an individual's performance can be predicted based on comparisons to groups of similar individuals. For example, power lifters have (or intend to develop) muscle performance similar to other power lifters. Likewise, endurance athletes have (or intend to develop) muscle performance similar to other endurance athletes. "Early birds" may benefit from different workout schedules than "night owls"; similarly, a user on diet restriction may require specialized pre-workout/post-workout meals.

In one exemplary aspect, the workout and readiness/recovery history for the population of users is analyzed to create one or more expected profiles. Each expected profile is associated with the heuristics and/or performance metrics for a subset of users having similar physiology and psychology. In one exemplary embodiment, the expected profiles are generated based on artificial intelligence (AI) and/or machine learning to identify similar users and their corresponding heuristics, rules, and/or patterns. While the exemplary embodiment is based on computer-assisted data science and data analysis techniques, other implementations may use human assessments (e.g., fitness experts, coaches, etc.) or some hybrid of human and machine learning. As described in greater detail infra, the initial expected profiles may be corrected and improved gradually over time as more and better crowd-sourced workout history is collected.

In one exemplary embodiment, a user may run through an initial assessment to grossly identify their "baseline" physiology and/or psychology. For example, establishing a baseline via an initial assessment may include one or more sets of squats, lunges, sit-ups, push-ups, pull-ups, abdominal rotations, a timed run, and/or a questionnaire (e.g., "how did you feel?", etc.) Completing the initial assessment provides baseline information as to the person's physiology (e.g., strength/stamina for each of the major muscle groups and/or cardiovascular endurance) and/or psychology (e.g., confidence, motivation, emotional state, etc.) In some cases, a user may be required to meet a minimum threshold of physiological and/or psychological performance for the assessment to be accurate. For example, a user that has never logged any workouts may be instructed to first establish a regular workout regimen before attempting assessment (e.g., "get in the habit of walking every day" before "run a timed mile.") Common metrics useful for generating a baseline or initial assessment may include, without limitation e.g., distance for an exercise (run, walk, bike, swim, etc.), repetitions accumulated, a particular pace threshold maintained for a specific duration, a minimum/maximum load, and/or any other physiological or psychometric metric.

In one embodiment, readiness and/or recovery metrics may be collected for an assessment period, obtained from historic tracking data, or inferred from existing schedule data. For example, nutrition information may be calculated based on meals that are logged by the user. Similarly, sleep tracking metrics may be retrieved via application programming interface (API) calls from a sleep tracking application. Still other implementations may infer sleep and/or nutrition based on the user's intended schedule and forecasted meal plan (e.g., 8 hours of sleep/day, 2000 calories/day).

Subsequently thereafter, the user may continuously update and/or augment input on their personal fitness goals and continue to track their workout history, sleep, nutrition and/or any other performance related data. Their baseline assessment, personal fitness goals, and/or ongoing workout history can be used to identify a matching expected profile. Subsequent workouts and/or other day-to-day activities can be recommended to the user based on the matching expected profile. Similarly, during a workout or other day-to-day activity, the user can receive dynamic feedback based on the expected profile; e.g., the user can be immediately notified and coached when they are over/under performing. In another such example, the user can receive dynamic feedback when they are staying past their optimal bedtime, skipping a meal, etc. In some cases, the user may be able to take corrective actions and/or accurately log their progress.

FIG. 1 is a graphical representation of user assessment (benchmarking), in accordance with the various principles described herein. As shown in FIG. 1, workout history is collected from a large population of users for an exercise (e.g., sit-ups, push-ups, squats, etc.) The workout histories are analyzed to generate a set of expected profiles. In this simple example, the expected profiles are shown in a two-dimensional "bubble chart" of maximum repetitions and maximum sets for an assessment exercise. More complicated embodiments may use a higher dimensional multi-variate analysis, the example of FIG. 1 being purely illustrative. Examples of variables that may be useful in a multi-variate analysis may include without limitation: age, sex, ethnicity, training load, training frequency, height, weight, sleeping habits, eating habits, and/or any number of other physiological and/or psychological parameters (e.g., behaviors, motivations, etc.).

Initially, the user benchmarks their performance in the assessment exercise. The user's performance is compared to the expected profiles; in this case, the user's performance 102A most closely matches expected profile: "profile 1". Profile 1 identifies the appropriate heuristics and/or performance metrics suitable for a subset of peers having similar e.g., physiology, psychology, and fitness goals. Notably however, as the user continues to regularly exercise and improve, their associated expected profile may change. For example, the user's performance metrics change over time (e.g., from performance 102A to performance 102B) and are associated with different expected profiles (e.g., profile 5, profile 6, . . . profile 14), these changes in expected profiles reflect the user's own personal fitness journey. Unlike conventional solutions that try to put every individual on a one-size-fits-all workout progression, the user's personal fitness journey changes the coaching and recommendations based on expected profiles that are most relevant to their current abilities and motivations.

Figure 2A:
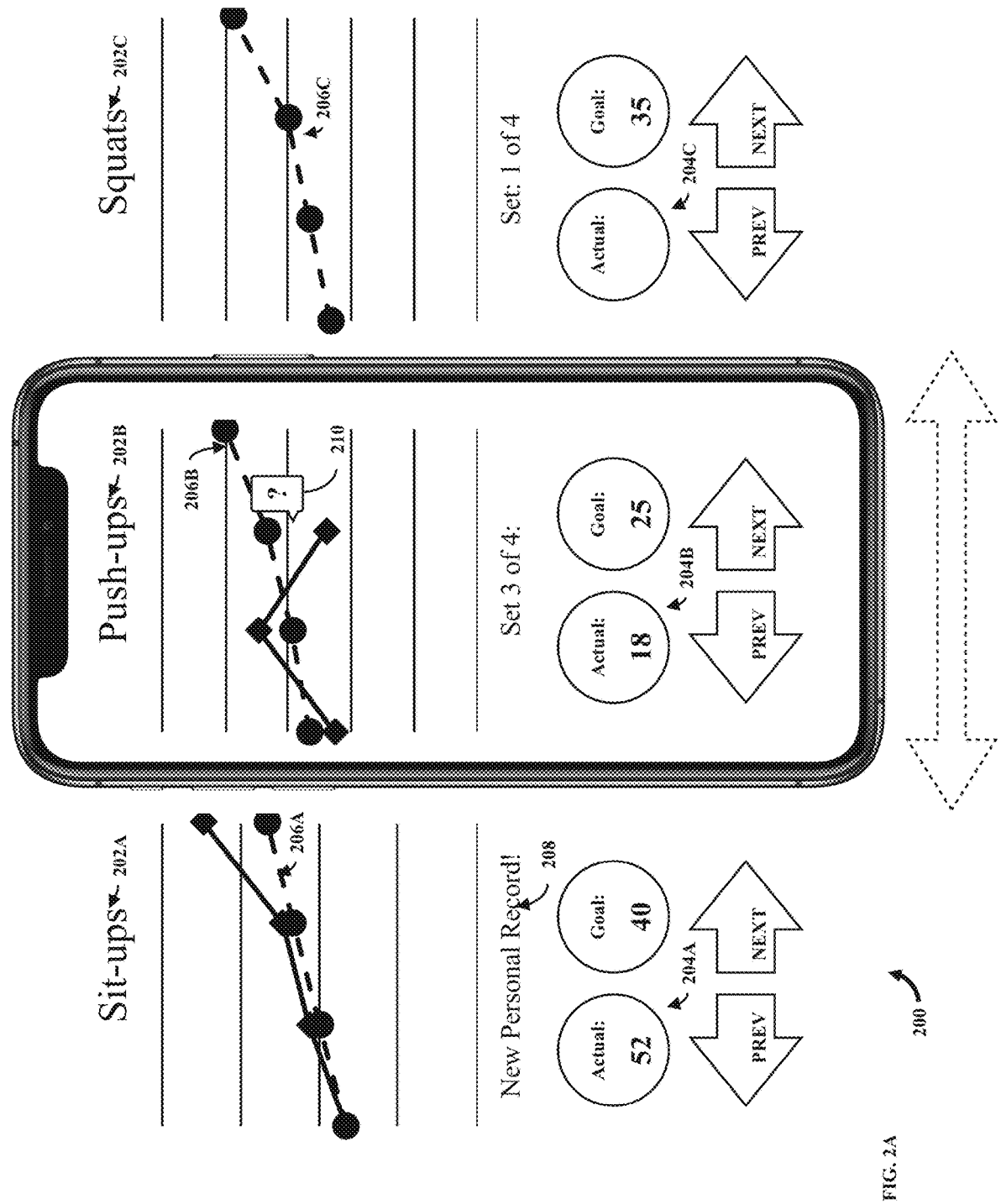
FIGS. 2A-2F are graphical representations of an exemplary workout coaching application, in accordance with the various principles described herein.

FIG. 2A illustrates one exemplary personalized workout recommendation and dynamic feedback user interface 200 based on workout history, readiness/recovery information, and/or personal fitness goals, consistent with the various principles described herein. As shown therein, the personalized workout recommendations are based on the heuristics and/or performance metrics associated with the expected profile and may be modified to incorporate readiness/recovery information. For example, the illustrated interface 200 recommends a set of exercises (e.g., "Sit-ups" 202A, "Push-ups" 202B, "Squats" 202C, etc.) and logs actual performance (204A, 204B, 204C) against an expected goal performance for the expected profile (206A, 206B, 206C). The user interface 200 may further include status e.g., a set count and/or motivational messaging ("New Personal Record!" 208).

A user may navigate the workout ("PREV", "NEXT") with virtual buttons. In the illustrated example, a user may also scroll through the workout using a horizontal user interface (UI) gesture (swipe back/forth) to select between activities. In some cases, the recommended workout may also provide the user with instructional information (e.g., exercised muscle group, proper form, why the exercise is important, etc.) In some embodiments, the interface 200 may be configurable based on user preferences. For example, a user may prefer vertical swiping in a "portrait" orientation (or change to a "landscape" orientation). Similarly, a user may prioritize, re-order, add, skip, start/stop timers, and/or remove workout recommendations. In some cases, a user may configure how workouts are displayed; for example, a user may prefer to see more or less detailed information e.g., bigger/smaller images, repetitions, weights, sets, distance, time, etc. Other variations of the interface 200 may be used with equal success.

Additionally, the exemplary user interface 200 can provide dynamic feedback 210 in response to such user input and/or during the workout. In some cases, dynamic feedback may be provided in response to skipping an exercise (e.g., "Why did you skip squats?"). In another example, as shown in FIG. 2A, a user that has failed to meet the expected performance may receive a notification (described in greater detail in FIGS. 2B-2C infra). Dynamic feedback may include a variety of different messages e.g.: interrogatory (e.g., "You have only completed 18 of 25 push-ups. How do you feel?), suggestions (e.g., "For this set, let's focus on form"), motivation (e.g., "You're doing great!"), information (e.g., "Push-ups in a wide stance or a narrow stance can activate different muscle groups"), status ("Only one more set to go"), etc.

While the illustrated embodiment uses visual feedback, other implementations may provide e.g., audible (voice, music, etc.) and/or haptic (vibration, etc.) feedback. Voice instruction, feedback, and/or commands may be useful where the user cannot directly touch the fitness tracking device. For example, during a push-up, the user's device may instruct the user to start a push-up with an audible "Down"; the user may respond with an audible "Up" to indicate the completion of a repetition. The user device may additionally provide feedback e.g., "That was too fast; for the next rep, slow down", etc. Similarly, haptic feedback may be useful for certain applications where the user can feel the device but need not directly respond (e.g., a smart watch may sense heart rate, and vibrate once a target heart rate has been reached, etc.)

Figure 2C:
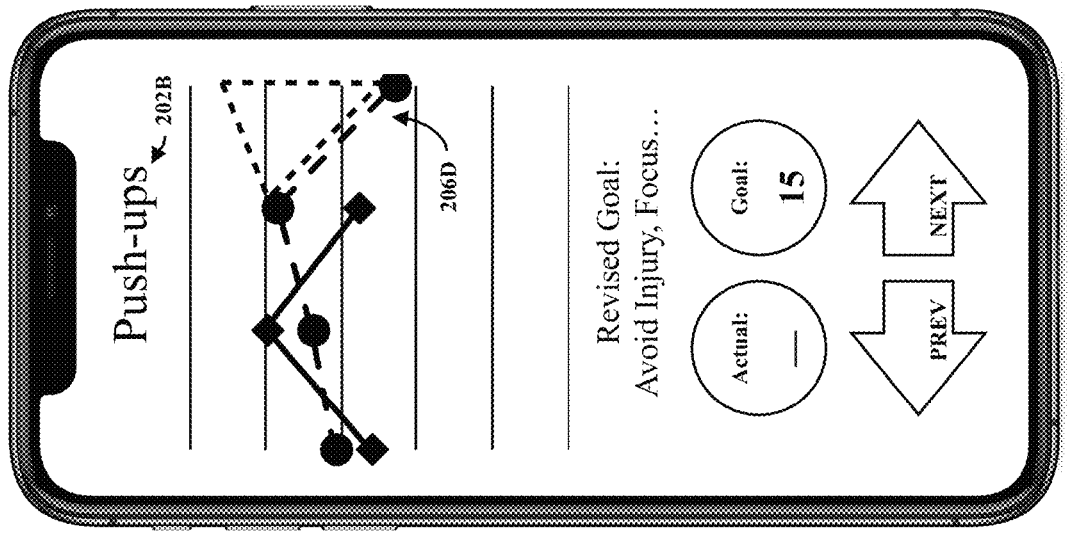
Figure 2B:
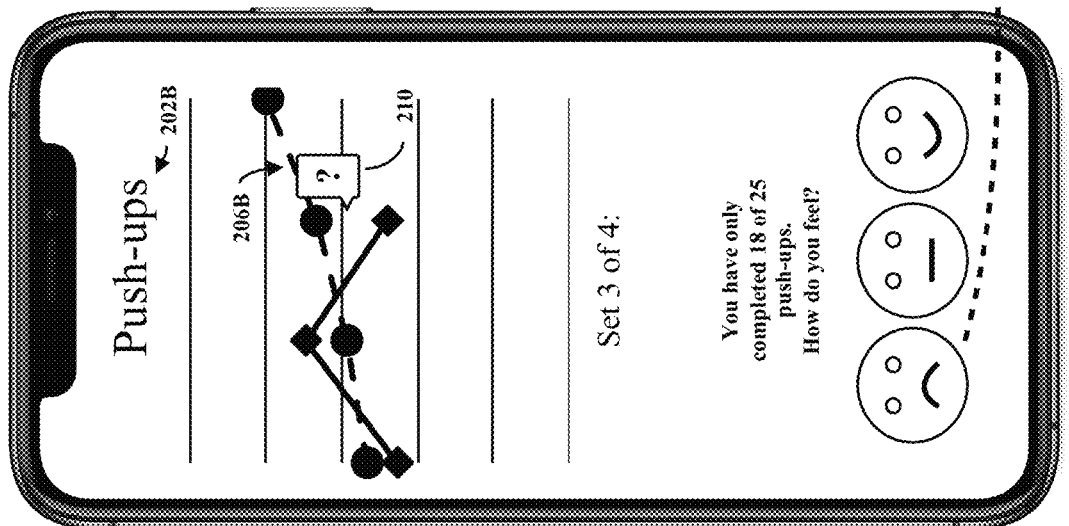

Referring now to FIG. 2B, one exemplary implementation of a dynamic feedback interface 220 is provided in greater detail. As shown therein, a user has failed to meet the expected performance. In the illustrated embodiment, the user device prompts the user to provide user input 210 to explain why. For example, a user may select a subjective emotional state (happy, indifferent, afraid of injury). In other cases, user input may be objective (e.g., injury, pain, inability, equipment unavailability, etc.) Still other types of user input may be provided, the foregoing being purely illustrative.

In response to user input, the user device adjusts the workout in accordance with the heuristics associated with the identified expected profile (revised interface 230 of FIG. 2C). In the example shown in FIG. 2C, the expected profile heuristics determine that the user's failure to meet expected performance is indicative of an increased risk of potential injury. Specifically, other users that are similar to this user and exercising under similar circumstances, are at increased risk of injury. Consequently, the workout is revised to an expected performance 206D such that the user can continue with a reduced goal; an informational note "Avoid Injury, Focus on Form" is also provided.

Notably, the heuristics for different expected profiles may vary widely; for example, a different heuristic could interpret the user's input as being indicative of lack of motivation. In response, the user device may offer more encouragement and/or suggest other more enjoyable activities. Still other heuristics may adjust subsequent workout stages so as to comply with a user's limitations; for example, a user that is taking longer than expected to finish the Push-up stage may be instructed to do a shorter run later on (so as to stay within a prescribed total workout time).

Once the user has completed the prescribed workout, the workout is logged appropriately (e.g., that the user revised the goal due to potential injury, and that the revised goal was met). In some cases, user input can be used to continuously improve the corresponding expected profiles and/or better match the user's performance with other expected profiles. In particular, users associated with an expected profile are treated similarly (e.g., prescribed similar workouts) because they are inferred to have similar physiologies and/or psychology. Performance progression for similar individuals results in positive feedback (further reinforcing the expected profile accuracy) whereas differences are negatively correlated (pushing users toward better fitting expected profiles). In other words, improvement to the user's classification and the expected profiles may be an emergent property of continuous user workout history analysis.

As previously alluded to, a user's schedule can affect workout performance in at least two (2) independent and distinct ways. Firstly, unlike physiological parameters which the user does not control (e.g., age, sex, height, weight, ethnicity, etc.) the user's day-to-day choices reflect their own agency. A user's behavior may be indicative of e.g., diligence, intensity, motivation, discipline, and/or other psychological states. For example, consistent detailed meal logging is characteristic of a much different psychological profile than inconsistent incomplete logging. Similarly, a user that regularly sleeps at 10 PM and wakes at 6 AM is likely much different in behavior than an irregular sleeper. Consequently, user scheduling information can be incorporated within the aforementioned expected profiles as part of the psychological parameters.

Additionally, the user's day-to-day choices directly impact their short-term performance. A user that does not adequately rest and re-fuel will have sub-optimal workouts and slower performance progression. To these ends, various embodiments of the present disclosure are directed to a holistic "program" that includes not only workout routine coaching (such as described supra), but also non-workout coaching. More directly, the expected profile can be extended to non-workout recommendations and/or dynamic feedback throughout their other day-to-day activities. The exemplary holistic program maximizes pre-workout readiness, enables dynamic coaching during workout routines, and/or intelligently manages post-workout recovery.

Figure 2D:
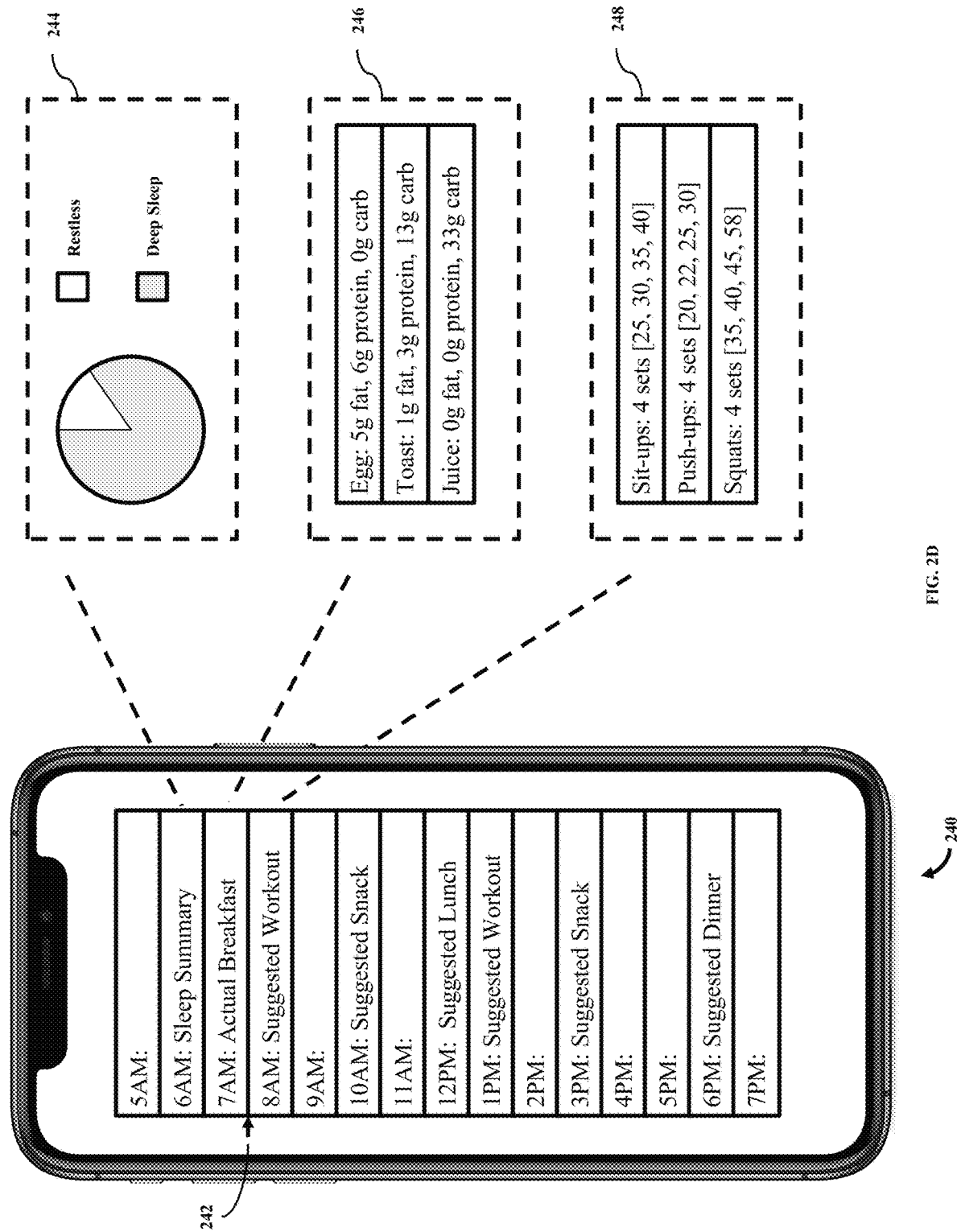

FIG. 2D illustrates one exemplary personalized fitness program user interface 240 based on workout history, readiness/recovery information, and/or personal fitness goals, consistent with the various principles described herein. As shown therein, the exemplary program view integrates with a user's existing calendar applications executed from their e.g., smart phone. The program view provides both recommended actionable items for activities in the future, and an actual record of logged actions for activities in the past (relative to the current time 242.) For example, a user may browse through their calendar to see how well they slept 244 (e.g., what percentage of their sleep was restless versus deep sleep), what they've eaten 246, and their upcoming recommended workout 248.

In one embodiment, the fitness program fits workout routines within the user's existing scheduling based on a complete picture of the user's current health (previous workouts, sleep, nutrition, etc.) and the user's associated expected profile. Readiness and recovery coaching before and after the workout ensure that the user is rested and refueled to receive the workout's maximum benefit (thereby speeding performance progression). As a practical matter, many users will encounter situations where they cannot get sufficient rest/nutrition; under these circumstances, the workouts can be modified to compensate for these deficiencies. In other words, the user may benefit more from completing a scaled back workout that accounts for their current physiological and/or psychological state than e.g., skipping the workout, or attempting an unrealistic workout.

As previously alluded to, the fitness program may incorporate information from a number of different sources. For example, a user may use a sleep tracking device to track their daily sleep cycle, a smart watch and/or smart shoe to track their workouts, and a smart phone to plan and log meals. Workout, sleep, and/or meal tracking data can be directly retrieved from the devices, and/or indirectly obtained e.g., access via 3$^{rd}$ party application programming interfaces (APIs). For instance, a sleep tracking device, smart watch, and/or smart shoe can provide data to a smart phone via health tracking APIs; the data may be made locally available to any appropriately permissioned health tracking application of the smart phone. Similarly, a meal tracking blog may provide external web portal interfaces to enable recipe query and nutrition information retrieval.

In other implementations, the fitness program may rely on user input (e.g., where the user manually logs their activities.) In some such variants, the fitness program may automatically populate meal, rest, and/or workout data records with recommended values that the user either confirms, rejects, and/or modifies. For instance, a sleep record may be populated with the recommended 8 hours of sleep from 11 PM to 7 AM; the user may accept the default sleep record or update the sleep record with their best estimate.

In one embodiment, the fitness program is seamlessly incorporated within the user's daily schedule for day-to-day activities. For example, the user's calendaring program may include a variety of personal and/or professional appointments as well as reminders or links for health and fitness activities (e.g., suggested meals/snacks, rest reminders, suggested workouts, etc.) In some cases, the calendaring application may directly launch the corresponding tracking application. For instance, a user may browse to their suggested meal and automatically launch their meal logging application to conveniently log their actual meal consumption. Similarly, a user may receive a sleep summary; if the user is interested, they can directly launch the sleep application to view their sleep summary.

Figure 2E:
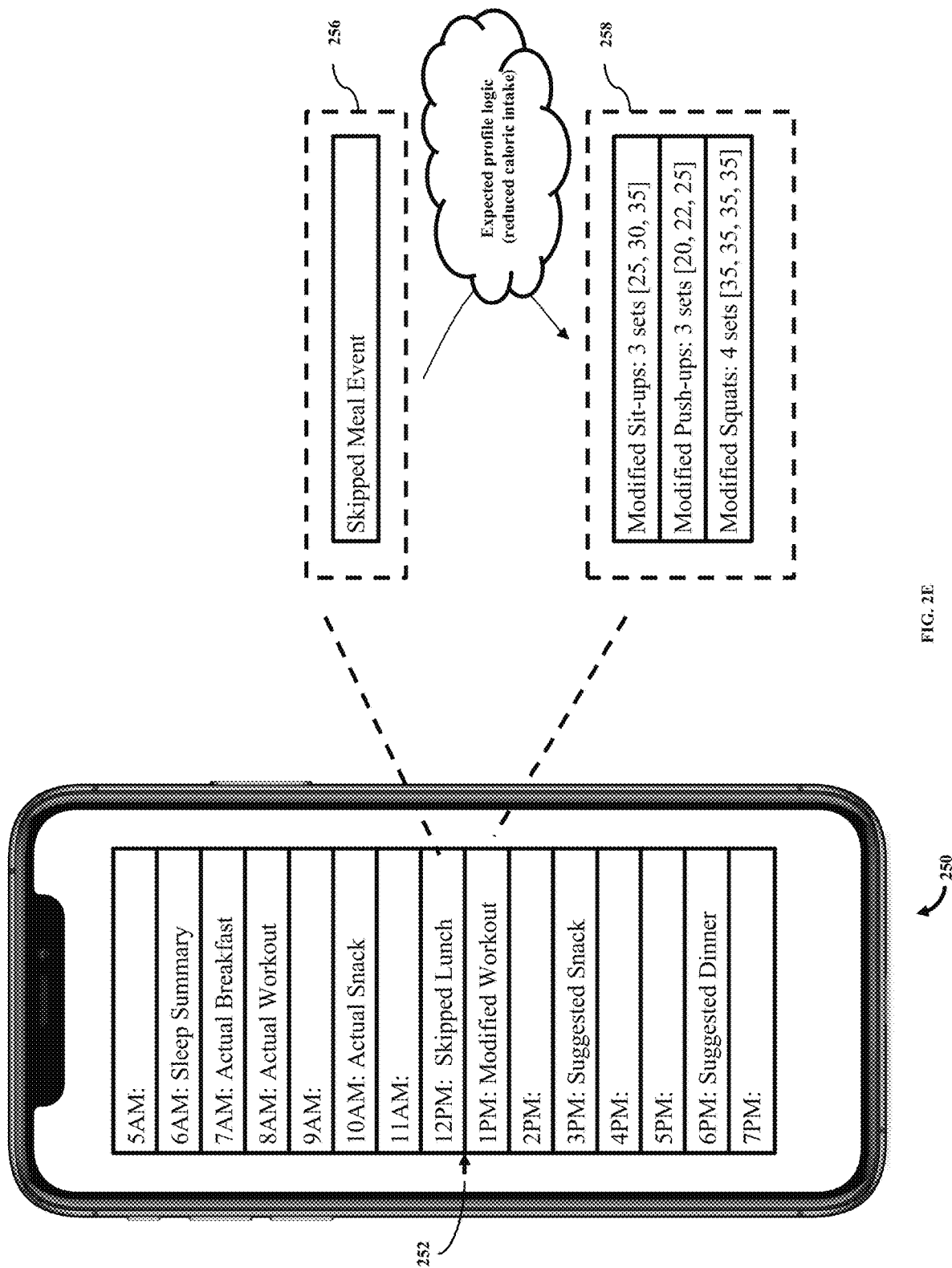

The holistic program enables dynamic modifications to workouts based on current user readiness metrics. For example, as shown in the exemplary personalized fitness program user interface 250 of FIG. 2E, at time 252, the user has skipped the suggested lunch (skipped meal event 256). Once the user decides to start their 1 PM workout, the workout 258 is dynamically modified to account for the skipped lunch event. In another such implementation, the fitness program may consider subjective reporting measures of readiness. For example, the user may be prompted to answer questions regarding e.g., soreness, energy level, mood, and/or sleep. Modifying the workout to account for reduced user readiness is more beneficial than e.g., skipping the workout or attempting an unrealistic workout (and risking injury).

In some embodiments, the user's actual sleep and/or nutrition data may be used to estimate e.g., muscle recovery, response times, awareness, blood sugar, estimated caloric availability/deficiency, hydration/re-hydration, etc. Specifically, the user's workout may be modified such that a population of similarly situated individuals (physiological and psychologically related peers) could reasonably be expected to derive benefit therefrom.

As but another such example, the user's calendar data and/or location data can be used to make trade-offs where necessary. For example, if the user is starting their workout late and has a hard stop, then the workout can be adjusted such that the user's most valued exercises (exercises that are most aligned with the user's goals) are prioritized and can be completed. Similarly, earlier start times (e.g., a longer workout duration) can be used to pack more exercises into the same time slot. Other considerations may include e.g., available equipment, nearby workout partners, commonly attended classes, etc.

Figure 2F:
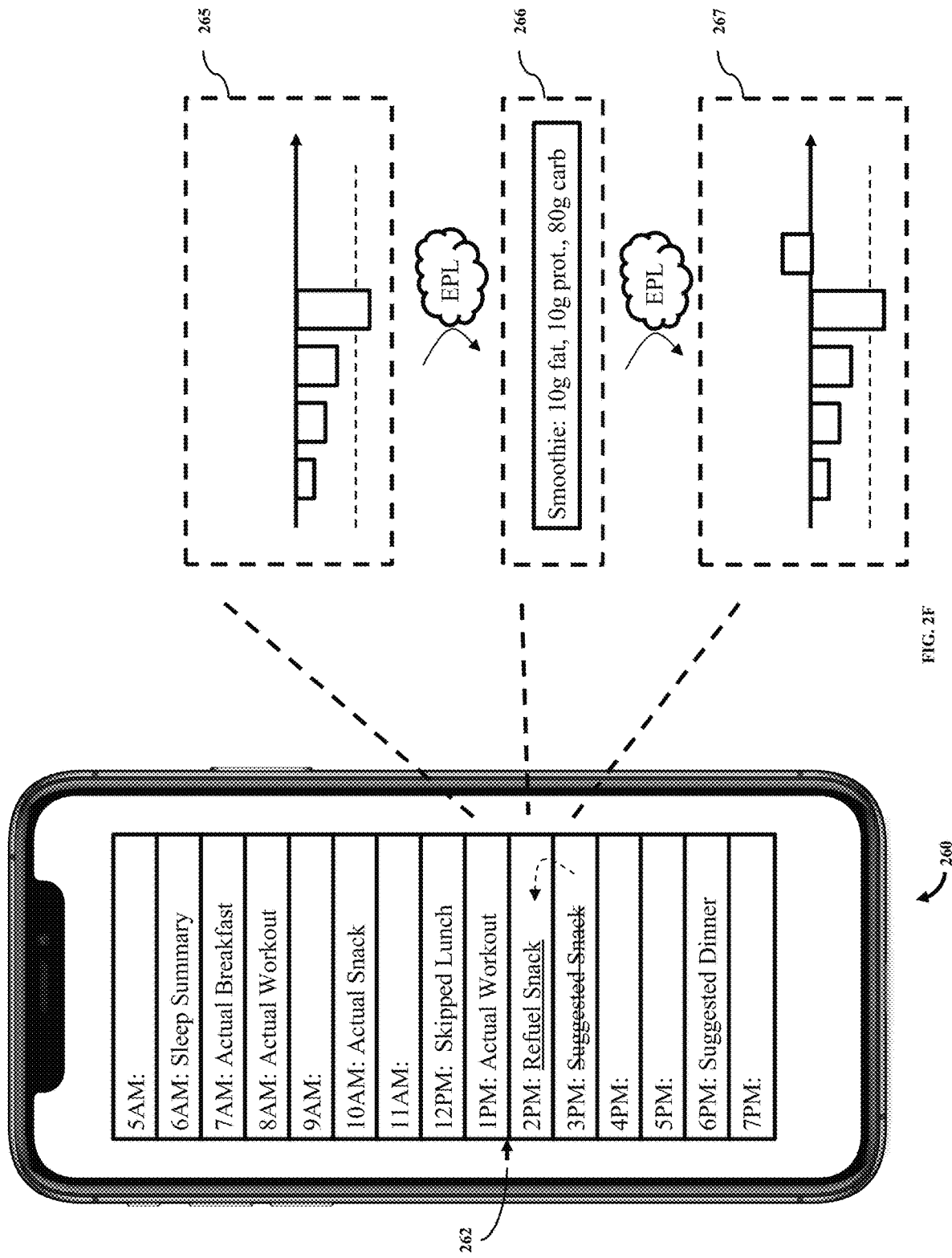

The holistic program also enables dynamic recovery coaching after workouts based on actual workout performance. For example, as shown in the exemplary personalized fitness program user interface 260 of FIG. 2F, at time 262, the user has skipped lunch and completed a modified workout. Unfortunately, the user has dropped into a caloric deficiency danger zone (as illustrated by the graph of caloric consumption over time 265). Caloric consumption may be estimated based on the actual workout metrics; more sophisticated variants may incorporate e.g., the user's physiology and metabolism.

The caloric deficiency event triggers an update to dynamic recovery coaching; responsively, the user is notified to consume their afternoon snack earlier. In some cases, the snack itself may be modified to provide e.g., more calories, a specific blend of macronutrients, etc. For example, the suggested refuel snack may be a much more substantial smoothie 266 (rather than a handful of nuts, etc.) When the user consumes the refuel smoothie, the caloric consumption graph is updated (the user exits the caloric deficiency danger zone 267). Alternatively, if the user does not consume a refueling snack (or refuels with a less substantial snack), then the user's recovery may be impacted. In some variants, the severity of impact may be estimated based on the expected profile modeling.

More generally, the disclosed embodiments of the present disclosure ensure that users receive instantaneous, accurate, and targeted feedback during workouts and/or other day-to-day activities which can greatly improve the performance progression. The disclosed solutions enable users to conveniently navigate their personal fitness journey. The foregoing discussion of the exemplary implementation is purely illustrative; artisans of ordinary skill in the related arts may add, remove, and/or substitute similar functionality, given the contents of the present disclosure.

Network Architecture

As previously alluded to, existing solutions have not addressed the holistic health and fitness of users. Consequently, different aspects of health and fitness have been historically isolated from one another in the consumer electronics space. For instance, sleep data, meal data, and/or workout data may be "silo-ed" into different consumer applications and/or device ecosystems. To these ends, various embodiments of the present disclosure aggregate health data from a broad variety of different sources (including 3rd party sources and/or legacy databases).

Figure 3:
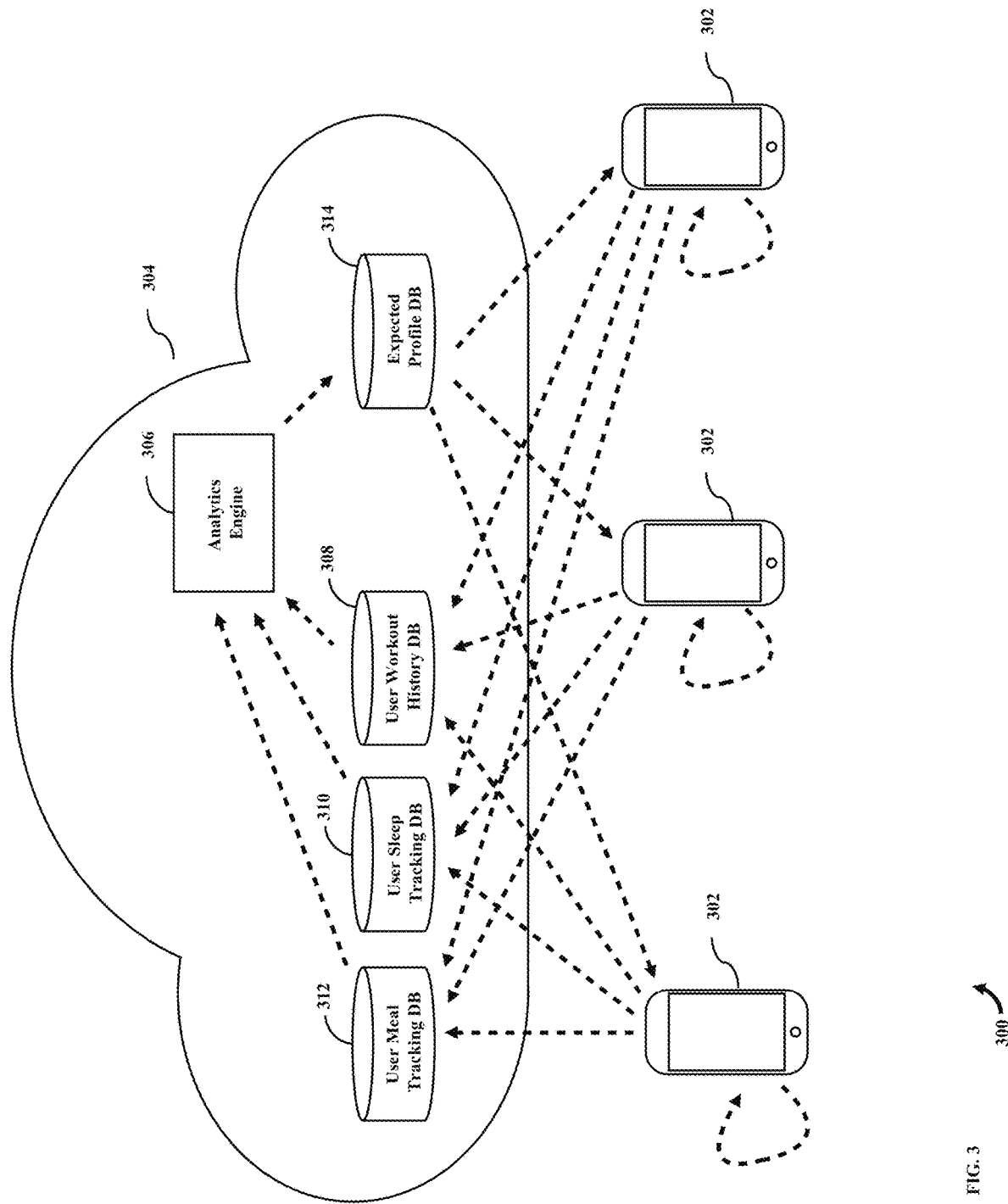
FIG. 3 is a logical block diagram of an exemplary network architecture configured to enable workout coaching based on workout history, readiness/recovery information, and/or personal fitness goals, in accordance with the various principles described herein.

Referring now to FIG. 3, an exemplary network architecture 300 configured to enable workout coaching based on workout history and/or readiness/recovery information is shown. As illustrated, the system 300 includes one or more user devices 302 in communication with a health tracking network 304. In one exemplary embodiment, the health tracking network 304 may include one or more of analytics engines 306 in communication with a user workout history database 308, sleep tracking database 310, meal tracking database 312, and a database of expected profiles 314.

The health tracking network 304 may include one or more wired and/or wireless, private and/or public network, including but not limited to, e.g., the Internet. The health tracking network 304 is, for example, a wireless local area network (WLAN), wireless wide area network (WWAN), wired network, or any other suitable communication channel. Accordingly, each of the user devices 302, analytics engine 306, and databases (e.g., user workout history database 308, sleep tracking database 310, meal tracking database 312, and expected profiles database 314) are configured with appropriate networking communication interfaces. An example of wired communication interface may include, but is not limited to, Ethernet; while examples of wireless communication interfaces may include, but are not limited to, near field communication (NFC), Bluetooth, Wi-Fi, 4G or 5G LTE. It is further appreciated that various gateways, routers, switches, base stations, and so forth may be involved in facilitating and forwarding communication between the foregoing devices. Additionally, it is noted that the foregoing health tracking network 304 may be itself, composed of several networks, such that the described components are distributed in various ones thereof. In alternative embodiments, the health tracking network 304 may include a series of devices communicating within software via software API's.

As used herein, the term "database" refers to a structured set of data records held within a non-transitory computer-readable medium and/or the mechanisms used to e.g., add, remove, modify, and/or query and retrieve the stored data records. The term "data record" refers to a collection of data structures that represent an association, grouping, organization, or other collection of information; common examples of data structures include without limitation: numbers (integers, floating point), values (Booleans, enumerations), characters, strings, arrays (1D, 2D, N×D, etc.), lists, hash tables, etc. For example, a database may be queried for one or more data records that satisfy a particular condition; e.g., containing a particular string, value, etc.

The user workout history database 308 stores a plurality of user data records and their corresponding workout data records. Each user data record may include detailed information with regard to e.g., accuracy of data, fitness goal definition, progression of performance, psychological parameters (e.g., behaviors, motivations, etc.), height, weight, age, sex, ethnicity, and/or any number of other user specific parameters. Each workout data record may include detailed information with regard to e.g., date/time of past exercises, scheduled date/time of future exercises, type and/or number of exercises, frequency of exercise, exerted muscle groups, duration of exertion, intensity of exertion, absolute load, relative load, range of movement, repetition, recovery time, fatigue, dynamic feedback/user response, frequency of revision, revision success/failure, and/or any number of other workout specific parameters. More generally, artisans of ordinary skill in the related arts given the contents of the present disclosure, will readily appreciate that virtually any data regarding either the individual users and/or their specific workout history can be stored.

The user sleep tracking database 310 stores user histories of sleep as sleep data records. Each sleep data record may include information with regard to e.g., date/time of sleep, suggested sleep time, actual sleep time, contiguity of sleep, irregularity of sleep, scheduled date/time of future sleep, quality of sleep (e.g., the clinical definition for sleep quality is based on the number and/or length of waking events), subjective user data (e.g., tiredness, time to alertness, etc.), and/or any number of other user rest parameters. As used herein, the term "sleep" generally refers to any rest event (e.g., naps, mid-day "siestas", etc.)

The user meal tracking database 312 stores user histories of consumption as consumable item data records and/or their constituent ingredients. Each consumable item data record may include information with regard to e.g., date/time of consumption, the suggested consumable and user modifications thereto, actual consumption, portion size, time interval over which the consumable was consumed (e.g., to estimate time varying effects), nutrient-related information, subjective user data (e.g., enjoyment, satisfaction, etc.), and/or any number of other user consumption parameters.

Common examples of nutrition-related information may include macronutrient information (e.g., calories, protein, fat, carbohydrates), micronutrient information (e.g., water-soluble vitamins, fat-soluble vitamins, minerals, fiber, water, etc.), allergen/intolerance information (e.g., lactose, gluten, peanut, etc.), ingredient type, ingredient size, portion size, and/or other food-related information. Consumable items may include single ingredient items (such as meat, fruit, vegetables, grains, etc.) as well as multi-ingredient items (e.g., recipes, menu items, meals, etc.). As used herein, the term "consumable" generally refers to foods, beverages, and other consumables such as vitamins, supplements, medications, etc.

The expected profiles database 314 stores heuristics and/or performance metrics for one or more expected profiles. For example, an expected profile may define a muscle group (e.g., abdominals), an associated exercise (e.g., sit-ups), and a workout with a series of expected performances and acceptable ranges (e.g., four (4) sets of increasing repetitions (25, 30, 35, 40) plus or minus 1 set, 5 sit-ups). Users that are associated with the expected profile should be able to meet the expected performances. Actual performance that deviates from the expected performance beyond an acceptable range may trigger execution of a heuristic and/or feedback. For example, a user that exceeds their expected performance range (e.g., performing 50 sit-ups where only 35-45 sit-ups were expected) may receive congratulatory feedback, a user that underperforms the expected performance range may be encouraged to improve and/or cause modification to subsequent workouts. In some cases, the heuristics may take user input into account, for example, a user that reports positively (e.g., "I've almost got it, let me try again") may have a smaller correction than a user that subjectively reports negatively (e.g., "I think that's all I got").

In one embodiment, the expected profiles database 314 additionally includes heuristics and/or performance metrics that enable modifications based on readiness. Modification rules may e.g., scale back or adjust acceptable tolerances based on certain conditions. For example, instead of requiring a sleep deprived user to do 4 sets, their workout may be scaled down to 3 sets. Similarly, a user that would normally have a tolerance of plus/minus 5 repetitions may be allowed a range of plus/minus 10 repetitions when they've skipped a meal. Other methods for increasing or decreasing workout intensity may include changing e.g., sets, repetitions, duration, rest intervals.

In some variants, the heuristics and/or performance metrics may account for differences in workout performance attributable to readiness (or lack thereof). For example, data analytics performed over a set of similarly situated and motivated users under varied readiness conditions (e.g., sleep deprived, underfed, etc.) may be used to generate expected profiles. Such profiles may be used to predict how the user will perform under analogous conditions and/or modify workouts accordingly.

In another embodiment, the expected profiles database 314 may include heuristics for post-workout recovery coaching. In some cases, recovery coaching may use actual logged workout performance to update the user's recovery program. As but one such example, a user that has had a particularly strenuous workout may be coached to consume a substantial post-workout snack. Similarly, rest and recovery messaging may be provided (e.g., "good job, remember to rest and refuel", etc.)

As previously noted, different human physiologies respond to rest and/or nutrition differently. Consequently, users with different fitness goals may be better served with different recovery strategies. The expected profile may describe optimal recovery strategies for the user (as determined by similarly situated peers). For example, a power lifter may need much more protein post-workout than an endurance athlete. Similarly, a performance athlete may be willing to eke out every ounce of gain using precise ramp-up preparation and taper down strategies before significant competition events.

It is appreciated that in the illustrated embodiment, the aforementioned databases (308, 310, 312, 314) are separate and distinct from the analytics engine 306 and/or user device(s) 302. However, in other variants, the databases may be incorporated in part or in whole with either the analytics engine 306 and/or the user device(s) 302 for storage thereat. For example, workout data records that have been logged (or scheduled) at a particular user device 302 may be stored locally until e.g., synchronized with the network (or vice versa). Additionally, or in the alternative, expected profiles (in whole or in part) may be stored at the analytics engine 306 and portions may be made accessible to particular devices 302 when queried and/or locally cached. Any combination of the foregoing configurations may be utilized with equal success.

While the foregoing example is presented in the context of strength training/calisthenic/cardiovascular type routines, artisans of ordinary skill in the related arts will readily appreciate that the various principles described herein may be readily adapted to virtually any activity e.g., sports activities, academics, hobbies, etc.

Methods

Figures 4A, 4B:
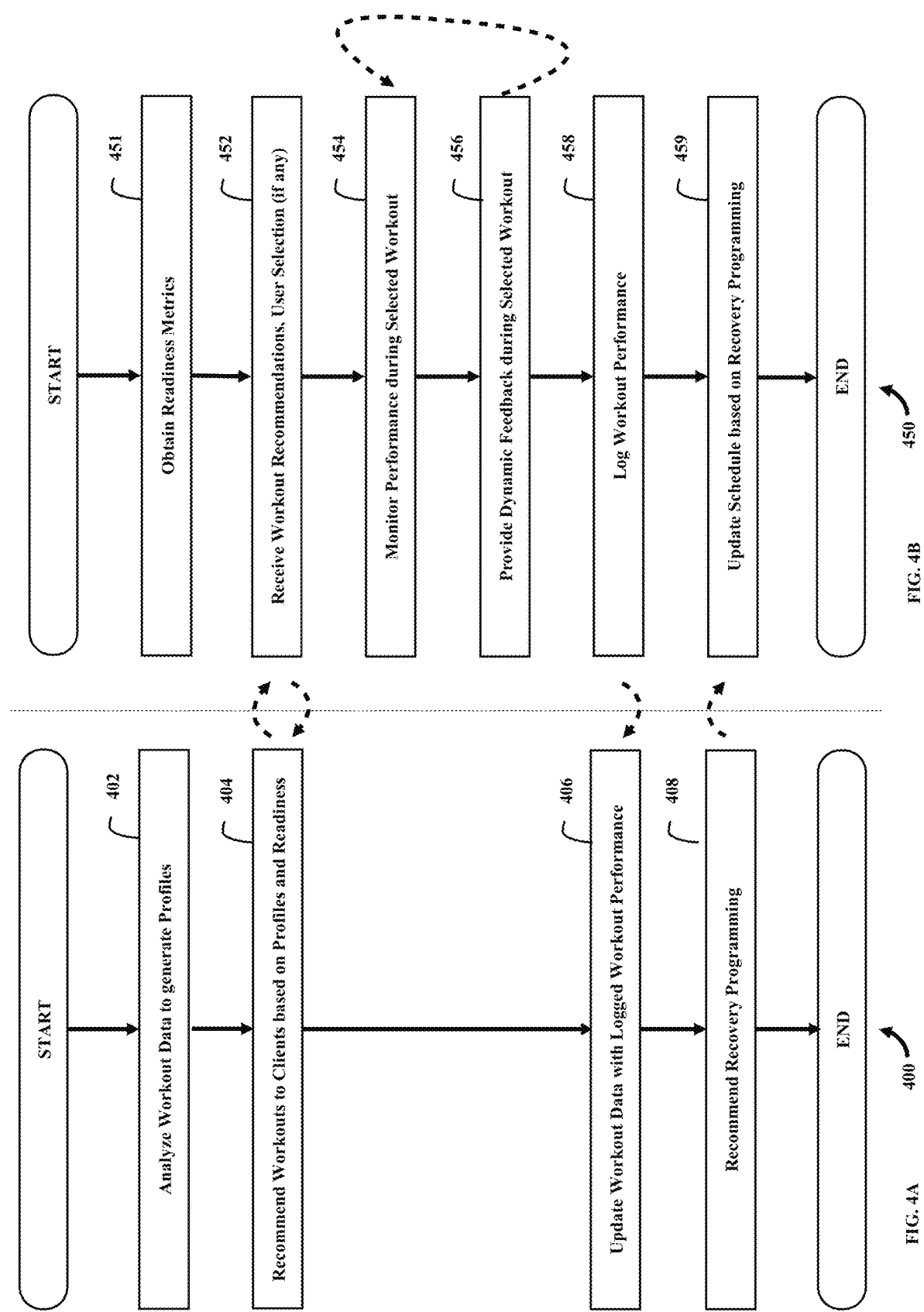
FIGS. 4A-4B are logical flow diagrams of methods for coaching a user based on workout history, readiness/recovery information, and/or personal fitness goals in a health tracking system, in accordance with the various principles described herein.

FIG. 4A is a logical flow diagram of an exemplary method 400 for providing workout routines to a user based on workout history and/or readiness/recovery information, in accordance with the various principles described herein.

At step 402 of the method 400, a health tracking system analyzes workout data and/or readiness/recovery information to generate one or more profiles. In one embodiment, workout data and/or readiness/recovery information for a large population of users is analyzed to classify users into "groups" that are physiologically and/or psychologically similar. In one exemplary embodiment, the identified "group" is analyzed to create an expected profile that parameterizes heuristics and/or performance metrics for its constituent members.

In one specific implementation, readiness/recovery information is analyzed to identify the short-term and/or long-term effects on individual performance. "Short-term", as used in reference to readiness and recovery herein, refer to time varying effects caused by physiological and/or psychological limitations of an individual. In contrast, "long-term" refers to the average capabilities and behaviors for an individual (the central tendency of a distribution). For example, different human physiologies metabolize nutrients at different rates. Even though two humans may both consume 50 grams of carbohydrates, the short-term spike in blood sugar is based on individual metabolism (which may vary widely based on human physiology). In contrast, the total number of calories consumed is an average property of human physiology (e.g., the metabolized calories distribution is centered around 450 calories). While long-term sleep deprivation and malnutrition certainly cause chronic health issues (where the performance of an individual decreases on average), these are fundamentally different from large (but temporary) variances in overall workout performance that may be attributed to short-term effects of insufficient rest and/or nutrition.

As used herein, the term "readiness" refers to user activities that occur prior to a workout that affect the user's short-term workout performance. For example, sufficient rest and nutrition immediately prior to a workout can maximize a user's motivation and caloric availability. In contrast, the term "recovery" refers to user activities that occur after a workout that affect the user's long-term performance progression. For example, habitually resting and refueling after a workout can improve muscle growth and metabolism trends over time.

While various embodiments of the present disclosure are discussed in the context of rest and nutrition (e.g., to optimize readiness and recovery), artisans of ordinary skill in the related arts given the contents of the present disclosure will readily appreciate that other non-workout activities may affect readiness and/or recovery, the foregoing being purely illustrative. Common examples of such non-workout activities include without limitation: hydration, meditation, mental preparation (e.g., team play reviews), circadian rhythms, mental and/or physical stressors (alcohol/caffeine/nicotine consumption, long work hours, etc.), hobbies, and/or other personal interests.

In another embodiment, workout data and/or readiness/recovery information for specific individuals is analyzed to identify physiological and/or psychological traits for that individual. For example, celebrities and/or athletes may have their own workout data and/or readiness/recovery information analyzed. The celebrity and/or athlete may then publish their workout data and/or readiness/recovery information such that other individuals can aspire to holistically steer their workouts and/or readiness/recovery habits to match the celebrity/athlete. More directly, even though a professional athlete may focus on strength training for specific muscle groups, an amateur may actually need to improve many different muscle groups (and/or when and how they eat/sleep) to achieve similar results. In other words, the celebrity profile can be used to dynamically coach a person toward an aspirational level of fitness of another person.

In still another embodiment, workout data and/or readiness/recovery information for a specific group of individuals may be analyzed. For example, an athlete may want to tailor their workouts and/or readiness/recovery habits to match against a peer set of specific athletes, e.g., a running back for a football team may want to know how they compare against all running backs in the league. Still other variants of the foregoing may be substituted with equal success, by artisans of ordinary skill in the related arts.

Referring back to step 402, the workout data and/or readiness/recovery information analysis can be performed via machine learning and/or other artificial intelligence (AI) techniques. Specifically, machine learning and/or artificial intelligence (AI) can be used to filter populations of users into subsets having similar characteristics. Each subset is associated with appropriate performance metrics based on e.g., workout and/or readiness/recovery history, interpolation/extrapolation from workout data, interpolation/extrapolation based on related muscle group exercises and workouts (e.g., pull-ups may enable some extrapolation to similar muscle exercises e.g., bicep curls, etc.) and/or user input/responses. In other implementations, performance metrics can be assigned based on expert human analysis or even explicit user responses/input (e.g., similar circumstances where users report similarly, etc.).

In one embodiment, the analysis generates one or more profiles. In one exemplary embodiment, profiles can be continuously updated based on crowd-sourced data from actual users. In other embodiments, the profiles may be generated initially, but subsequent data analysis and profile updates are triggered based on threshold events (e.g., based on excessive deviation, etc.) Still other techniques may perform analysis on a periodic basis, aperiodic basis, etc.

In one exemplary embodiment, the analysis may be subdivided into "stages" of analysis; for example, the analysis may need to identify which subsets of user workout and/or readiness/recovery data should be grouped together and/or what patterns and relationships exist in the subsets of user workout and/or readiness/recovery data. In another example, analysis may be iterative over time. For example, as user adoption increases and workout and/or readiness/recovery data continues to accumulate, data analysis may be repeated so as to continuously improve the accuracy and/or robustness of the profiles.

As used herein, the terms "analyze" and "analysis" refers to any technique, method, process, algorithm, and/or system that examines a data set to extract relationships from the data set. Analysis may be manual (e.g., entry based on human analysis), automatic (machine learning), or a hybrid thereof (e.g., software identification with human acknowledgement, etc.) More generally, artisans of ordinary skill in the related arts given the contents of the present disclosure, will readily appreciate that virtually any scheme for data analysis may be substituted with equal success the following being purely illustrative.

As a brief aside, humans are good at interpolating and/or extrapolating relationships in relatively small amounts of data. Traditional examples of such relationships include, without limitation: predictive relationships, causative relationships, correlative relationships, statistical behavior, probabilistic behavior, and/or any arithmetically defined function. However, human analysts are expensive to employ and are poorly suited for analyzing large, "noisy", multi-variate data sets. Additionally, certain types of data analysis are "mining expeditions" that are commercially infeasible to pursue with human labor e.g., the result may be too low yield, unpredictable, sparse, etc. Recently, however, advances in data science and machine learning have enabled automated identification and recognition of patterns in data sets. Computer-based data analysis greatly expands the breadth and/or depth of relationships that can be identified in large data sets.

Machine learning algorithms vary widely in their approach, data requirements, and tasks/capabilities. Machine learning typically involves creating a model, which is trained to process data to make predictions therefrom. Common examples of machine learning models include e.g., artificial neural networks, decision trees, support vector machines, Bayesian networks, genetic algorithms, and hybrids thereof. Common techniques for training include supervised learning, unsupervised learning, reinforcement learning, feature learning, sparse dictionary learning, anomaly detection, multi-variate association, etc.

In one embodiment, different types of data may be analyzed with different types of machine learning. For example, user classification may be based on supervised learning, whereas heuristic and performance metric generation may be based on unsupervised learning. As a brief aside, supervised machine learning uses training data to infer relationships where the input and output data types are known. Supervised learning models may be particularly suitable for e.g., identifying which users should be grouped together under an expected profile because training data can include clear examples of endurance athletes, sprint athletes, etc. In contrast, unsupervised machine learning can be used to identify patterns in unstructured data (e.g., where there is no clear definition of "input" or "output"). In other words, once the users for an expected profile have been identified, unsupervised learning may be used to "mine" for unknown characteristics about the users to generate heuristics and performance metrics for the expected profile.

There may be a myriad of situations that require further derivation, inference, exploration, and/or feedback because the machine learned relationships are ambiguous or inaccurate. In such cases, it may not be possible to classify the data with machine learning, without further human assistance (e.g., user input, expert analysis, etc.) For example, a user may need to provide additional feedback via explicit input, a fitness test, sport evaluation, or otherwise provide proxy data (data representative of an immeasurable quality) useful to support more accurate user profiling. In other cases, a physician or sports expert may be able to identify intangible factors that lay outside of the collected data.

In another such example, user classification can be continuously improved based on new information using reinforcement learning. More directly, once a user has been associated with an expected profile, the resulting actual workouts logged by the user can be used to further reinforce (or weaken) the strength of both the user's match and/or the expected profile. In other words, the classification of a user should change as the user's personal fitness journey changes. User progression obviously benefits the user but may also be used to further tune the health tracking systems classification, coaching, and/or recommendation accuracy.

Still other techniques for data analysis using machine learning may be added, modified, substituted, parallelized, and/or sequentially cascaded, by those of ordinary skill in the related arts, given the contents of the present disclosure.

Referring back to step 402, various embodiments analyze workout and/or readiness/recovery data to extract relevant patterns in physiological and/or psychological data. Common examples of workout data may include, without limitation: fitness goal definition, progression of performance, muscle group, duration of exertion, intensity of exertion, absolute load, relative load, range of movement, repetition, recovery time, psychological parameters (e.g., behaviors, motivations, etc.), height, weight, age, sex, ethnicity, and/or any number of other user specific workout parameters. Common examples of readiness and/or recovery data may include, without limitation: date/time of sleep/consumption, suggested sleep time/consumable items, actual sleep time/consumption, contiguity of sleep, irregularity of sleep, quality of sleep, portion size, time interval over which a consumable was consumed, nutrient-related information, and/or any number of other subjective user data.

More generally, however, any parameter that affects user performance may be considered. For instance, environmental conditions may affect human physiology and/or psychology. Such environmental factors may include e.g., elevation, temperature, humidity, sound (music), other people (workout buddies), season, and/or any number of other considerations. As but one example, a user that lives at sea level may perform differently (and thus require different coaching) when they are at a different elevation.

Due to the sensitive nature of user data, various embodiments of the present disclosure may additionally anonymize certain information. In one exemplary embodiment, the user may select what information may be analyzed. In some variants, the user may be able to protect personally identifying information (name, height, weight, age, sex, etc.) In some variants the user may be able to protect workout related information (e.g., time, location, duration, frequency of workout, etc.) As but one example of anonymization, identifying information may be unidirectionally hashed, scrambled, encrypted, and/or otherwise obscured.

In alternative embodiments, user identifying information may be used e.g., to improve accuracy. For example, a first set of profiles may be generated from anonymized user workout data for users that do not want to release sensitive information and a second profile may be generated from private user workout data for users that waive their privacy. The second profile may offer additional benefits and/or better coaching based on the improved specificity. For example, location and/or demographics (age, ethnicity, sex) information may provide better psychographic profiling useful for niche motivational messaging.

In order to prevent malicious activity (e.g., polluting performance metrics with misreporting, etc.), the user may be required to verify their authenticity in order to e.g., create user accounts and/or generate workout data. For instance, the user may be required to provide proof of existence (via e.g., an external email account, phone number, or other personal verification method). Additionally, in some cases, a user account may be validated to ensure that the user profile information is reasonable. For example, age, height and/or weight inputs may be verified to lie within the realm of possibility. In some cases, external verification of personhood may require certification (trust credentials) or other root of trust (e.g., trusted 3rd party verification, etc.) Still other techniques for managing user database integrity may be substituted with equal success by artisans of ordinary skill in the related arts.

As used herein, the term "workout" refers to one or more activities performed by the user with measurable physiological and/or psychological impact. Examples of measurable physiological impacts may include without limitation e.g., cardiovascular strain, heart rate, caloric consumption, muscular exertion, fatigue, blood oxygenation, lactate production, blood occlusion, nervous system activation, temperature increase, sweat production, changes to form/body positioning (via video analysis), audible data (exhalations, foot strikes, etc.), and/or any other physical effect of exertion. Physiological data may be collected via one or more sensors and/or the user device interface (e.g., buttons, touch screen, microphones, etc.). Common examples of sensors include e.g., accelerometers, heart rate monitors, blood sensors, microphones, cameras, etc.

As used herein, "performance" and "performance metrics" refer to any set of workouts and/or predicted/expected physiological and/or psychological impacts for similar users based on e.g., physiology, psychology, fitness goals and/or any other relevant parameters. As used herein, the term "performance progression" is used to refer to a user's tolerable physiological and/or psychological impact as a function of time. For example, a user's physiological progression may be measured as a function of e.g., changes to heart rate as a function of distance run over multiple workouts, changes to maximum repetitions/sets of a load over multiple workouts, etc. Notably, while performance progression is generally measured physiologically, psychological measures may also have significant value. For example, some users may subjectively enjoy working out regardless of whether or not they improve their physiological performance. Also, a user's psychological impact may cause changes to motivation and/or outlook when they hit a physiological "plateau."

In one exemplary embodiment, heuristics refers to any logic that is configured to dynamically respond to user input. In one exemplary embodiment, the heuristics are conditional rules for execution by a processor of the user device. As used herein, the term "conditional" refers to any action or event that is subject to one or more logical conditions or requirements being met. Common examples of conditional rules include e.g., "if-then", "only-if-then", "do-until", "perform-while-true", "case(s)", and/or other Boolean logic. While the conditional logic is described herein, artisans of ordinary skill in the related arts given the contents of the present disclosure will readily appreciate that non-Boolean based rules may be substituted for conditional rules with equal success. Common examples of non-Boolean rules include without limitation: machine learned rules, pattern-based rules, predictive rules, weighted rules, "fuzzy" logic, and/or other techniques.

At step 404 of the method 400, the health tracking system recommends workouts to clients based on the expected profiles. In one embodiment, workout recommendations may be based on the expected profile and one or more of e.g., user data records, workout data records, subjective user input, sleep data records, consumable item data records, environmental factors, advertising, or other health tracking system processes. In one exemplary embodiment, the expected profiles may be associated with heuristics and/or performance metrics that enable the client device to identify salient events and/or provide dynamic feedback in view of the recommended workout. Each recommended workout may identify one or more exercises, the expected performance corresponding thereto, and/or the conditions under which the user has deviated from expected performance.

For example, a client device may receive a workout that prescribes a set of exercises, an expected number of sets/repetitions, and/or rules for adjusting the workout if the user is underperforming due to injury, soreness, energy, mood, sleep, nutrition, or lack of motivation ("readiness adjustments"). In other embodiments, the health tracking system may push a number of workouts to a client device that are generally associated with the user's closest matching expected profile. When the user wants to do a workout (or schedule a workout for later), they can select one of the pushed workouts.

In one exemplary embodiment, the workout recommendations may be adjusted for the user's readiness by the client device (readiness metrics may be locally stored for e.g., privacy, connectivity reasons, etc.) In one such variant, the workout recommendations may include heuristics that define how the workout recommendations may be adjusted for the user's readiness. The heuristics may describe increasing or decreasing workout intensity (e.g., sets, repetitions, duration, rest intervals, etc.) based on readiness metrics (described in greater detail infra).

In another exemplary embodiment, a set of workouts may be "pulled" by a client device based on e.g., user parameters, the user's profile, previous workout history, or other client-side considerations. For example, a user may walk into their gym and identify equipment that is available (e.g., treadmills, kettlebells, and seated row) and/or their total time for working out (e.g., 45 minutes), responsively the health tracking system can identify workouts for the expected profile that best match the user's specified criteria and readiness (soreness, energy, mood, sleep, nutrition, etc.) In another such case, a set of workouts may be pulled based on user input; for example, a user that has injured themselves (or cannot complete an assigned workout) may pull alternative workouts for their expected profile. Similarly, a user that has to adjust their workout intensity may need to get different workout routines mid-workout for their expected profile.

In some cases, a super set of workout suggestions may be pushed to a user and cached for internal retrieval. In one example, a user may generally receive a suggested set of routines that should be completed within e.g., a week. Any of the workouts can be locally queried, scheduled for activity, and/or logged at the client device without requiring further health tracking system interaction. In another example, a user may be "cusping" from one expected profile to another. The health tracking system may push suggested workouts that are associated with both profiles. Thereafter, the client device may be able to dynamically bridge between the suggested exercises during the user's workouts, thereby smoothly transitioning the user throughout their personal fitness journey.

In some situations, a hybrid of "push" and "pull" may be used. For example, a user may pull a first set of workouts, and be pushed a second set of workouts based on the expected profile; e.g., a user may request upper body workouts, which additionally cause lower body workouts to be delivered in tandem. In other cases, a user that requests a workout may be suggested with alternative workouts so as to vary a user's workout schedule. For example, a user that has explicitly selected a "20-minute walk" may be pushed other workouts having similar effect (e.g., "mild calisthenics").

While the foregoing example is presented in the context of a health tracking system and client device interaction, artisans of ordinary skill in the related arts will readily appreciate that workouts may be provided via alternative sources and/or avenues. For example, a client device may send/receive workouts to/from other client devices and/or other parties; e.g., a smartphone that is paired to a smartwatch can provide workouts thereto. Similarly, a user may be able to send recommended workouts to a training partner, etc. In some cases, user transfers may occur in a broadcast or multicast manner; for example, a coach may send a team of athletes a set of workouts. Each athlete may have their own set of workouts further personalized based on their specific needs.

At step 406 of the method 400, the health tracking system updates the workout data with logged performance. As used herein, "log" and/or "logging" refers to any addition, derivation, inference, and/or subsequent manipulation of data records directed to user activity. Logging may be manual (e.g., entry by a user, personal trainer, coach, and/or other human), automatic (machine entry via e.g., client device, health tracking server, 3$^{rd}$ party service, etc.), or a hybrid thereof (e.g., machine logged with human acknowledgement, etc.) More generally, artisans of ordinary skill in the related arts given the contents of the present disclosure, will readily appreciate that virtually any scheme for logging may be substituted with equal success, the following being purely illustrative.

In one embodiment, workout data records are received from the client device and associated with the user profile. In one exemplary embodiment, the workout data record includes e.g., time and/or date of workout, detailed information with regard to e.g., type and/or number of exercises, exerted muscle groups, duration of exertion, intensity of exertion, subjective user input, and/or any other workout specific data. Additionally, the user data record may include any salient events e.g., where a heuristic was triggered and/or performance metric was exceeded/not met by a prescribed range. Salient events and/or dynamic feedback may include e.g., substitute exercises, added/removed exercises, completion status, duration, physiological and/or psychological impact and/or other user input. For example, a user may additionally add personal notes and/or user tags (e.g., "Personal Best", "Strained hamstring on 3rd set", etc.)

Dynamic feedback and/or readiness information for users may be an important source of information for updating expected profiles. Empirical evidence suggests that while user subjectivity varies between individuals, it is generally consistent over time for the same individual (e.g., a user that underreports discomfort is likely to consistently underreport, etc.) Consequently, various exemplary embodiments of the present disclosure may use subjective data (user input) to further improve the heuristics and performance metrics associated with expected profiles. In some cases, subjective reporting may be difficult for non-human interpretation. Thus, some variants may provide anonymized user input to a human (e.g., a physical therapist, etc.) for interpretation, validation, verification, and/or translation into objective metrics for updating expected profiles.

In other embodiments, dynamic feedback to workouts and/or readiness information may be specific to a user. For instance, the user may be able to "opt out" of providing subjective input, and their workout and/or readiness information data records may be excluded from expected profile updates. Non-disclosed user input may detract from the accuracy and/or quality of a user's feedback. Validation and/or verification of non-disclosed user input may be unnecessary. Similarly, some variants may additionally allow for post-workout logging. In some cases, the post-workout logging may be manual and/or user specific; in other cases, the post-workout logging may be automatic based on conditional rules.

In some embodiments, the user profile may be updated based on analysis of the user's workout, sleep, and/or consumable item data records. For example, a user that consistently falls below their personal health and fitness goals may receive encouragement and/or feedback to re-evaluate their goals. In some cases, user workout, sleep, and/or consumable item data records may be matched against expected goals to ensure that adequate progress is being made. Logging is prone to error and/or misreporting; e.g., some users may consistently under/overreport their workout, sleep, and/or nutritional regimen. Analyzing a user's own performance against the expected performance metrics of an expected profile may assist in user expectations and/or correct for misreported data. For example, a person that is consistently overreporting their workouts may show subpar performance gains. Under such situations, the health tracking system may further adjust the user's profile consistent with a different expected profile and/or remind the user that tracking efficacy is based on diligent record keeping.

At step 408 of the method 400, the health tracking system recommends recovery programming to clients based on the expected profiles and the logged workout performance. In one embodiment, recovery programming recommendations may be based on the expected profile and one or more of e.g., workout data records, sleep data records, consumable item data records, environmental factors, advertising, or other health tracking system processes. The recovery programming may identify actionable items for activities in the future. Common examples of actionable items include without limitation: sleep items (time and/or quality), nutrition items (amount, macronutrients, timing, etc.) and/or heuristics for estimating variances in performance attributable to insufficient readiness and/or recovery practice.

For example, a client device may receive a fitness program that prescribes e.g., times for resting, meals for consumption, workouts and/or rules for adjusting the program if the user is underperforming due to lack of rest and/or nutrition. Thereafter, the client device can adjust the fitness program to emphasize sleep times if the user is not getting enough rest or add/remove snacks or meals based on nutritional requirements.

In some cases, a super set of actionable items may be pushed to a user. As but one such example, a user may receive a calorically dense meal (for high caloric availability), a high protein meal (to assist in muscle recovery), and a low-calorie meal. Thereafter, the fitness program selects one of the meals based on the user's actual behavior (e.g., high performance, moderate performance, or skipping).

FIG. 4B is a logical flow diagram of an exemplary method 450 for coaching a user with dynamic feedback, in accordance with the various principles described herein.

At step 451 of the method 450, a client device obtains readiness metrics. In one exemplary embodiment, the client device prompts the user for subjective input regarding soreness, energy level, mood, and/or sleep. In another embodiment, the client device collects the readiness metrics locally at the client device. In one exemplary embodiment, local collection may include monitoring user activity and/or soliciting the user for input. For example, a smart phone can track a user's day-to-day activities via application programming interface (API) integration with the user's calendaring program.

In other embodiments, the client device may obtain readiness metrics from other devices of the user's community of personal devices. As used herein, the term "personal device" refers to a set of devices associated with a user. The user's community of personal devices may have many different functionalities that satisfy different useful niches with regard to personal health and fitness tracking. For example, a smart phone may enable a user to log meals and/or schedule their day-to-day activities. A smart watch may allow a user to capture movement, monitor heart rate, and/or track sleep. Still other variants will be readily appreciated by artisans of ordinary skill in the related arts, the foregoing being purely illustrative.

In one exemplary embodiment, the client device may use hierarchical logic to determine which readiness metrics should be used and/or preferentially weighted from the community of personal devices. In some cases, the hierarchical weighting may be static (or set to a default configuration); for example, a smart shoe may be preferred for workout data, a smart watch may be preferred for sleep tracking, and a smart phone may be preferred for meal tracking. In other variants, the hierarchal weighting may be flexibly configured e.g., by the user, client device, and/or fitness tracking system. For example, a user may prefer to use the step count provided by a smart watch, rather than a smart phone, etc. Similarly, the client device and/or fitness tracking system may preferentially prefer data from certain devices due to e.g., manufacturing quality, business considerations, and/or other device specific considerations.

In some embodiments, the client device can provide the readiness metrics to a health tracking system to assist in workout recommendations and/or readiness adjustments. In other embodiments, the client device can store the readiness metrics (e.g., for privacy, connectivity reasons, etc.) and perform workout modifications locally.

Still other embodiments may provide a subset of readiness data. For example, the user may only wish to expose a certain subset of historic data (e.g., the user may only wish to include sleep data, but not meal tracking data). In another such example, historic data may have diminishing value as a function of time; for example, user data beyond a few days may have little (or no) readiness value.

At step 452 of the method 450, the client device obtains workout recommendations and/or readiness adjustments from a health tracking system. In some cases, the client device may directly provide the workout recommendations to the user. In other cases, the client device may consider other client-side considerations to further winnow down recommended workouts. For example, a user may locally impose restrictions (e.g., no workouts longer than 45 minutes, ignore workouts when outside of a geo-fenced "home gym" area, ignore workouts during injury/recovery periods, etc.)

In one embodiment, the workout recommendations and/or readiness adjustments may be received from a health tracking system based on the user's profile and/or one or more closely matching expected profiles. In other embodiments, the workout recommendations and readiness adjustments may be further filtered by the client device based on client-side information (e.g., user schedule, available equipment, user mood, etc.) e.g., to focus on the subset of workouts that the user is interested in. Still other embodiments may hybridize client-side and server-side considerations. For example, the user may frequently pick their own workouts, while still being open to workouts recommended based on expected profiles.

In some embodiments, the client device may receive workout recommendations and heuristics to locally perform readiness adjustments. As previously noted supra, the heuristics define how the workout recommendations may be adjusted for the user's readiness e.g., increasing or decreasing workout intensity, dynamic coaching, etc. based on readiness metrics. As but one such example, the client device may privately store the user's readiness metrics (e.g., sleep and/or meal tracking data); the client device can use the heuristics to modify workouts recommendations based on readiness metrics, without exposing sensitive user data. In another such example, the client device may have intermittent connectivity (e.g., trail runs, extended backpacking, etc.) Local copies of the heuristics enable the client device to dynamically modify workouts recommendations using readiness data even in very remote locations.

Once a workout is recommended, adjusted, and/or selected, the client device monitors performance during the selected workout and provides dynamic feedback (if necessary) at steps 454 and 456 of the method 450. In one embodiment, the user may input workout data into the client device and receive dynamic feedback via a visual user interface. In one such variant, the user interface may be a natively executed application running on a user's device (e.g., smart phone, watch, laptop, etc.). Other common embodiments may use a web browser, or other intermediary web portal located at home or at a gym. Users may use a screen, keyboard, and mouse or other computer peripherals to interact with the displayed workout (e.g., to see the various exercises, input repetitions/sets, etc.)

In other embodiments, the user may provide auditory input to the client device and receive dynamic audible feedback therefrom; e.g., the client device may read workout instructions aloud and/or accept voice commands. For example, the client device may instruct the user to start a push-up with an audible "Down"; the user may respond with an audible "Up" to indicate the completion of a repetition. In a similar embodiment, haptic type interfaces may use accelerometers and/or haptic feedback to communicate with the user. For example, the client device may vibrate to instruct the user to start a repetition, the user's motion (captured via accelerometer) may indicate completion of a repetition. Still other types of user interface may be substituted by artisans of ordinary skill in the related arts, given the contents of the present disclosure.

In one embodiment, the client device monitors for salient events and/or conditions where a heuristic was triggered. For example, the heuristic can specify an expected performance metric within a prescribed range. Other common examples of heuristics may include without limitation e.g., completion of an exercise too quickly/slowly, heart rate being too high/low, irregularity of form, excessive/minimal strain (via blood occlusion, oxygenation, lactate, etc.), and/or any number of other indicia.

As but one example, the heuristic may specify a number of repetitions; the client device counts repetitions, if the user cannot meet (or exceeds) the specified number of repetitions, then the client device provides dynamic feedback and/or modification to the recommended workout (e.g., by increasing or reducing the next set's repetitions). In another such example, the heuristic may specify an expected time of completion (e.g., each repetition/set should be completed within a time window), failure to remain within the time window may be indicative of fatigue or incorrect form. Still other examples may monitor a user's psychological state; for example, a user that is tired early may be allowed to cut their workout short to prevent injury, or urged to complete the entire workout, depending on the expected profile's psychometric rules.

In one embodiment, the heuristic and/or dynamic feedback may be based on the readiness metrics. Consider a situation where the user has skipped a meal, the client device can infer that a dip in workout performance is due to the caloric deficiency and may dynamically advise the user to have a quick drink of a sports beverage (or similar calorie boost). Similarly, a user that is subjectively reporting that they have low energy may underperform; depending on the heuristic, the client device can adjust the workout intensity or provide dynamic motivation that is more in line with the user's current energy level.

In some embodiments, the user may enable, disable, and/or postpone dynamic feedback. For example, some users may find dynamic coaching distracting during an exercise, but may be interested in receiving feedback later (e.g., during a rest period, etc.) In these circumstances, the client device may track status, but only provide feedback when the user expressly wants to know how they did. In another such example, some users may not want dynamic feedback in the form of coaching but are open to changes to the workout routine. In some such variants, the user may be able to see when and why the workout changed (if interested).

In some cases, dynamic feedback may additionally reference and/or pre-populate feedback based on pre-workout or post-workout activities. For example, a user that did not sleep well prior to exercise may receive informational messaging regarding the importance of sleep. Similarly, under performance that is attributable to a caloric deficiency or dehydration may remind the user to eat a post-workout snack or drink. In some cases, multiple events may be referenced and/or pre-populated. For example, due to biological absorption constraints (e.g., 20-40 g of protein per hour), a hard workout may impact multiple snacks/meals. A 2-hour high intensity workout may call for a post-workout shake with 20-40 grams of protein and, 60-90 min later, a protein-augmented lunch ("eat an additional 20-grams of protein at lunch"). Similar considerations may apply for sleep, etc.

In still other embodiments, a user may be able to provide their user to another user. For example, a user may want to provide their dynamic feedback to a personal trainer. In this manner, the user may benefit from personal trainer advice without paying the personal trainer to watch them exercise. Similarly, the personal trainer may be able to remotely coach a much larger clientele.

In one embodiment, subjective user reporting is incorporated as part of the dynamic coaching experience throughout the workout; for example, a user may be prompted to provide e.g., rate of perceived effort (RPE) assessments throughout the workout. The RPE input may be used to adjust workout intensity. In some variants, RPE reporting is triggered based on overperformance or underperformance relative to the recommended workout. For example, a user that has failed to meet their prescribed number of repetitions is prompted to report their RPE; the RPE can be used in conjunction with the user's expected profile to provide dynamic feedback and/or workout modification. In still other variants, RPE reporting may be provided at the end and incorporated with the workout data records for post-workout analysis.

In some embodiments, the client device may initiate subjective user input reporting based on e.g., the user's expected profile. In other embodiments, subjective user input reporting may be configured by a $3^{rd}$ party. For example, a coach can insert user reporting events for a coached athlete to ensure that the athlete remains on track. Other common examples of $3^{rd}$ parties that may be appropriately permissioned to request user input include without limitation: teammates, personal trainers, and/or training partners.

The user's subjective input may be used to improve future workout recommendations. For example, a person that routinely underperforms due to lack of readiness or failure to maximize recovery can be shifted to a slower progression track. In another such example, user input can be used to shift workout scheduling e.g., to ensure that the user is adequately rested and/or fed before and after workouts.

Various other schemes for monitoring a user's progress in view of an expected profile will be readily appreciated by artisans of ordinary skill, given the contents of the present disclosure.

At step 458 of the method 450, the client device logs the user's actual workout data. In some embodiments, the user may be prompted to reconcile monitored exercise with the actual exercise performed. For example, a user may have been recommended an exercise, but decided to do something else (due to injury, equipment availability, mood, etc.) In other examples, the client device's sensors may be unable to accurately gauge completion, inaccurate, and/or faulty. The actual workout data records should only reflect what the user completed (or failed to complete). Actual user workout data may be stored as user workout data records, which may be stored at either or both of the client device and/or the health tracking system.

In some embodiments, a user may be able to locally access their user workout data records. In some cases, the user's immediate access to previous user workout data records may be useful to e.g., track progress, plan for future workouts, and/or used for other motivational purposes. In some cases, the user workout data records can be made accessible via e.g., external application programming interfaces (APIs) to a variety of other tools.

At step 459 of the method 450, the user's schedule is updated with recovery programming. In one embodiment, the recovery events may be informative messaging and/or reminders (e.g., "good job, remember to rest and refuel", etc.) In some embodiments, the recovery events may include actionable items. For example, recovery programming might include actionable items for e.g., sleep and a snack.

In one exemplary embodiment, actionable events may include any of e.g., time and/or date, detailed requirements with regard to the actionable event (e.g., required sleep duration, required sleep quality, macronutrient requirements, hydration amounts, etc.), informational messaging, acceptable substitutions, and/or any other recovery specific data. For example, a user that has completed a particularly strenuous exercise may have sweated more than expected; as a result, the user is provided with an actionable event to rehydrate (e.g., drink 16 oz of water, within an hour). In another such example, a sleep deprived user that did not meet their expected performance may be provided with an actionable event to get to sleep earlier; similarly, a user that skipped a meal before running may be prescribed a more substantial post-workout refuel snack (or in some cases, multiple snacks/meals).

In some embodiments, the recovery programming may be adjusted for the user's particular requirements by the client device (based on client-side considerations, etc.) In one such variant, the recovery programming may include heuristics that define how the recovery programming recommendations may be adjusted for the user's considerations. For example, heuristics may describe substitutions between different macronutrients (e.g., protein for fat or carbohydrates, and vice versa). In another such example, the heuristics may provide the user with different options e.g., high protein for muscle recovery, high fat for sustained energy, etc.

Additionally, as previously alluded to, recovery habits may have short-term and/or long-term effects. Consequently, recovery items may only be valid during a specified time window. In such cases, recovery programming may expire (a user that cannot refuel within a certain time window may miss out on optimal performance regardless of subsequent consumption).

Other common examples of client-side considerations may include without limitation: available time and/or resources, other scheduled tasks, subjective user input, convenience, business considerations, etc. For example, a user may receive an eight-hour sleep action item; the sleep item may be flexibly scheduled based on the user's existing schedule (e.g., a bedtime reminder is calculated based on a client-side alarm setting). Similarly, a user may receive a suggested meal item but need to modify the ingredients based on e.g., what they currently have available in their pantry. As but another such case, informational messaging may be tied to promotional offers (e.g., "to get the most out of your workout, grab a protein shake at the gym.")

In some embodiments, actionable items may include subsequent reporting back to the health tracking system. Subsequent reporting may include data regarding the user's subsequent activity (e.g., completion, percent adherence, skipped, etc.) For example, a user that is prescribed a post-workout snack and rest may be assessed for adherence to the suggestions. In some cases, adherence data can be useful for updating the user's profile.

More generally, artisans of ordinary skill in the related arts will readily appreciate that a wide expanse of usability may be necessary with individualized user workouts and/or readiness/recovery programming. In an ideal world, every workout can be perfectly logged, yet real world considerations exist. While accuracy is important, "perfect" adherence is not required for user benefit; "good enough" may suffice to keep users on their personal health and fitness journey.

While the foregoing examples are presented in the context of a single workout, artisans of ordinary skill in the related arts, given the contents of the present disclosure, will readily appreciate that a workout regimen can be steered over time so as to enable a user to achieve particular fitness goals. As but one example, a casual athlete user (e.g., classified in a first expected profile) might have a goal to improve their sport performance in view of a sports idol (e.g., a second expected profile.) The most realistic way for the casual athlete user to achieve their goals may be greatly affected by their physiological and psychological characteristics. In some cases, similarly situated and motivated users may have greater success by e.g., focusing on physiological goals (e.g., working on one muscle group before another, focusing on flexibility, etc.) and/or psychological goals (e.g., establishing a regular workout discipline, pushing through discomfort, etc.) In other words, steering users to improve and transition to new expected profiles may be more efficient to achieve performance progression than others.

Apparatus

FIG. 5A is a logical block diagram of one exemplary server apparatus 500, useful in accordance with the various principles described herein. In one embodiment, the server apparatus 500 includes a processor 502, non-transitory computer-readable medium 504, and one or more network interfaces (e.g., a first network interface 506, and a second network interface 508).

The components of the exemplary server apparatus 500 are typically provided in a housing, cabinet or the like that is configured in a typical manner for a server or related computing device. It is appreciated that the embodiment of the server 500 shown in FIG. 5A is only one exemplary embodiment of a server 500 for the health tracking system. As such, the exemplary embodiment of the server 500 described herein with reference to FIG. 5A is merely representative of any of various manners or configurations of servers or other data processing systems that are operative in the manner set forth herein.

The processing circuitry/logic 502 of the server 500 is operative, configured, and/or adapted to operate the server 500 including the features, functionality, characteristics and/or the like as described herein. To this end, the processing circuit 502 is operably connected to all of the elements of the server 500 described below.

The processing circuitry/logic 502 of the host server is typically controlled by the program instructions contained within the memory 504. The program instructions 504 include a workout coaching application that enables dynamic feedback as explained in further detail supra. The workout coaching application at the server 500 is configured to communicate with and exchange data with the client-side workout coaching application running on a processor of the health tracking devices. In addition to storing the instructions 504, the memory 504 may also store data for use by the health tracking program. As previously described, the data may include the user data records, the user workout data records, sleep tracking data records, meal tracking data records, and/or expected profiles.

The network interfaces of the server 500 allows for communication with any of various devices using various means. In one particular embodiment, the network interface is bifurcated into a first network interface 506 for communicating with other server apparatuses and a second network interface 508 for communicating with user devices. Other implementations may combine these functionalities into a single network interface, the foregoing being purely illustrative.

In one exemplary embodiment, the first network interface 506 is a wide area network port that allows for communications with remote computers over the Internet (e.g., external databases). The first network interface 506 may further include a local area network port that enables communication with any of various local computers housed in the same or nearby facility. In at least one embodiment, the local area network port is equipped with a Wi-Fi transceiver or other wireless communications device. Accordingly, it will be appreciated that communications with the server 500 may occur via wired communications or via the wireless communications. Communications may be accomplished using any of various known communications protocols.

In one exemplary embodiment, the second network interface 508 is a network port that allows for communications with a population of health tracking user devices. The second network interface 508 may be configured to interface to a variety of different networking technologies consistent with consumer electronics. For example, the network port may communicate with a Wi-Fi network, cellular network, and/or Bluetooth devices.

In one exemplary embodiment, the server 500 is specifically configured to analyze workout data records and/or readiness/recovery information from a number of users to generate expected profiles that describe e.g., the physiological and/or psychological behavior of similar users in terms of heuristics and performance metrics in accordance with the principles described above. In particular, the illustrated server apparatus 500 stores one or more computer-readable instructions that when executed enable e.g., analyze workout data records and/or readiness/recovery information from a population of users to generate profiles, recommend workouts to users based on the profiles and/or readiness metrics/heuristics, update workout data records with logged performance, and update user scheduling based on recovery programming.

FIG. 5B is a logical block diagram of one exemplary user apparatus 550, useful in accordance with the various principles described herein. In one embodiment, the exemplary user apparatus 550 includes a processor 552, non-transitory computer-readable medium 554, a network interface 556, a user interface 558, and sensors 560.

In one exemplary embodiment, the user devices 550 are configured to monitor a user's workout progress and/or readiness/recovery metrics and dynamically provide feedback in accordance with an expected profile. User devices 550 may also be referred to herein as health and/or activity monitoring devices, or client devices. The user devices 550, in one exemplary implementation, include one or more portable computerized devices that are configured to e.g., recommend, display, monitor, feedback, motivate, and/or otherwise provide workout information to a user. In an exemplary embodiment, the specific workout information that are displayed may include the exercise, current progress, expected progress, and/or any dynamic feedback associated therewith.

In one exemplary embodiment, the user devices 550 are additionally configured to enable a user to log actual workout activity. The user devices 550 may include one or more portable computerized devices that are configured to measure, obtain, monitor, generate, collect, sense, or otherwise receive physiological and/or psychological impact experienced by a user. In an exemplary embodiment, the specific data that are collected may include e.g., repetition count, set count, duration, as well as physiological information such as e.g., heart rate, blood oxygenation, carbon dioxide production, lactate production, blood occlusion, nervous system activation, sweat, blood sugar, etc.

In some embodiments, the user devices 550 may include a variety of sensors 560 including, without limitation: accelerometers, heart rate monitors, cameras, microphones and/or other sensing mechanisms (e.g., blood monitors, etc.) For example, a client device may use an accelerometer to e.g., count steps, repetitions, monitor motion (e.g, form). Similarly, blood oxygen sensors can detect e.g., blood oxygenation, lactate production, etc. Cameras can be used to monitor changes to form/body positioning (via video analysis), and microphones can be used to capture audible data (exhalations, foot strikes, etc.)

In one variant, certain ones of the user devices 550 may include wearable health-related parameter measurement and computing devices, such as e.g., a smart watch, an activity tracker, a heart rate monitor, a sleep tracking device, a smart scale, and/or smart eyeglasses. In addition, an exemplary user device 550 may include a smartphone having one or more of the foregoing capabilities and/or which enables user entry of the foregoing workout data. Alternatively, the user device 550 may be in communication with a health and/or activity monitoring device.

Other examples of health parameter data may include data that the particular device 550 is configured to collect (such as athletic activity, biometric information, and environmental data). For example, an activity tracking device may be configured to collect activity data such as steps taken, distance traveled, rate or pace of a run, and/or flights of stairs climbed, etc.; a heart rate monitor may be configured to collect heartbeat data; a sleep tracking device collects data relating to how much time a user/wearer spends sleeping; a nutrition tracking device collects data relating to food and drinks consumed by a user; a smart scale collects data relating to a body weight, body fat percentage, and/or body mass index (BMI), etc. Furthermore, a smartwatch and/or smartphone, may be utilized as an activity tracking device, a heart rate monitor, a sleep tracking device, and/or a nutrition tracking device. The user device 550 may comprise any of the foregoing types of devices and/or may receive collected data from a first device at one or more applications running on the user device 550.

The exemplary user device 550 may be further configured enable entry and/or display of collected data. In such instances, the exemplary user device 550 may run one or more applications configured to process (e.g., transform) the collected data. Exemplary applications include e.g., UA Record™, MapMyFitness®, MyFitnessPal®, Endomondo®, etc. each owned by the Assignee hereof. Other health activity related monitoring applications may additionally be utilized in connection with the present disclosure, such as those specifically designed to receive information from a particular type of health monitoring device (e.g., a $1^{st}$ party application which is published by the device manufacturer, or $2^{nd}$ party (trusted) or 3rd party (untrusted) applications designed to work in conjunction therewith); the foregoing being merely representative of the general concepts of the present disclosure.

Additionally, in one exemplary embodiment the application(s) running at the user device 550 includes a workout coaching application that enables dynamic feedback in accordance with an expected profile and/or readiness/recovery information. The workout coaching application enables a user to receive workout recommendations and/or log workout activity. As discussed in greater detail supra, the workout coaching application enables a user to manage their workout regimen via communication to and/or coordination with a network side application run at the health tracking server 500.

In one exemplary embodiment, the exemplary user device 550 is specifically configured to provide dynamic feedback based on an expected profile and/or readiness/recovery information in accordance with the principles described above. In particular, the illustrated user device 550 stores one or more computer-readable instructions that when executed are configured to cause the user device 550 to e.g., obtain readiness metrics, obtain workout recommendations and/or readiness adjustments from a health tracking system, monitor performance during the selected workout and provide dynamic feedback (if necessary), log the user's actual workout data, and update the user's schedule with recovery programming The above described system and method solves a technological problem common in industry practice related to individually tailoring workout recommendations for individual users with different physiological and/or psychological traits. The above-described system and method improves the functioning of the computer/device by recommending workouts to the user based on collecting workout data and/or readiness/recovery information from a population of similarly situated individuals and ensuring that the user can receive dynamic feedback in accordance with an expected performance.

Portions of the system and methods described herein may be implemented using one or more programs or suitable software code, such as the workout recommendation application on the health tracking device and the health tracking program on the server, both described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer-readable medium can be, by way of example, only but not by limitation, an electronic, magnetic, optical, electromagnetic, infrared, or semiconductor system, apparatus, system, device, or computer memory. The computer-readable medium may include multiple computer-readable media storing computer executable instructions, such as in a distributed system or instructions stored across an array. A "non-transient computer-readable medium" may be any type of data storage medium that can store computer instructions, including, but not limited to the memory devices discussed above.

FIGS. 6A-6D depict graphical representations of an exemplary user interface, consistent with the various principles described herein.

Figure 6A:
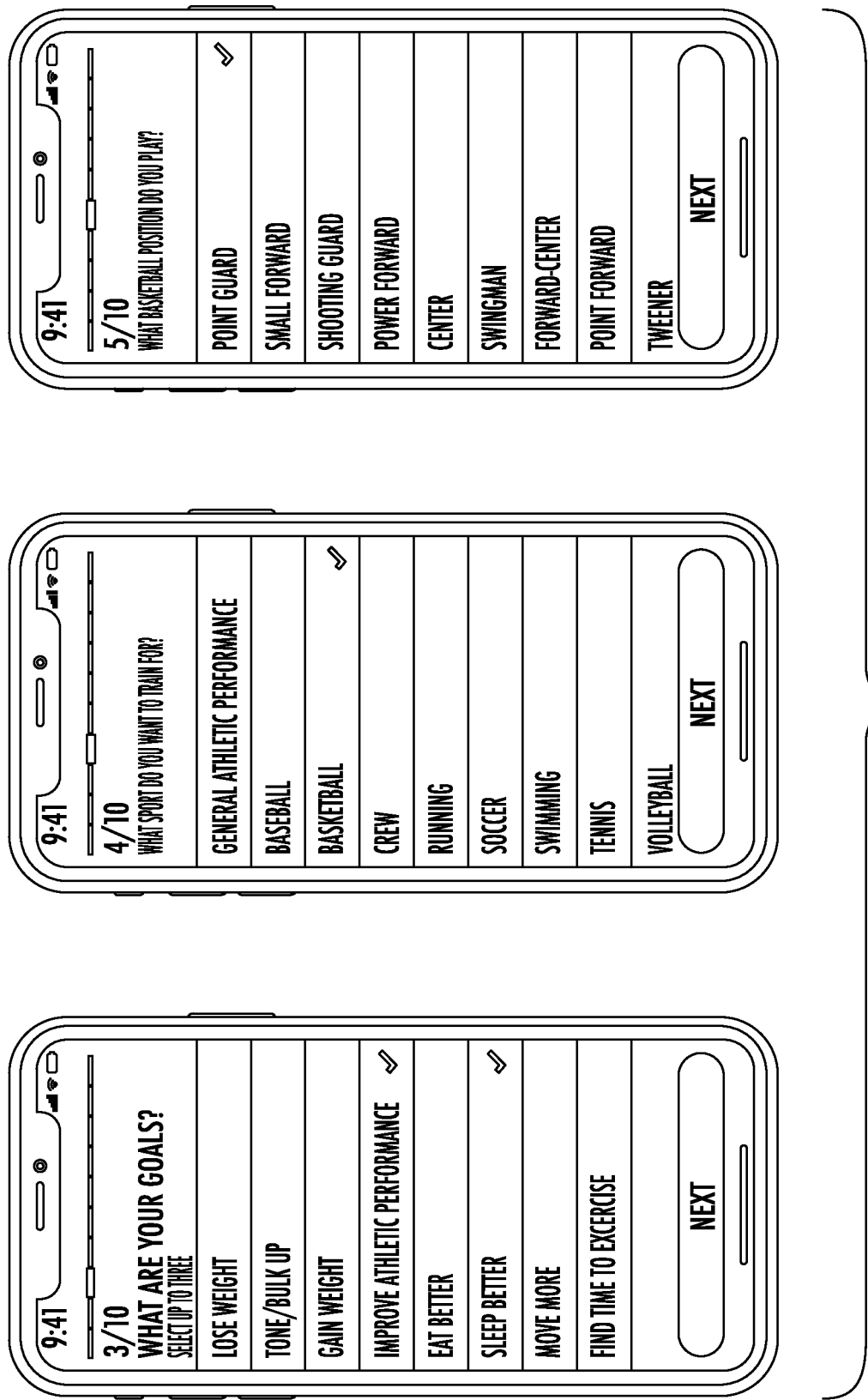

FIG. 6A illustrates a user interface for requesting user input regarding their personal fitness goals during onboarding. The user input can be used for initial assessment, baselining, and profile construction. In some cases, the information enables the health and fitness tracking system to tailor content and target products that users are interested in.

Figure 6B:
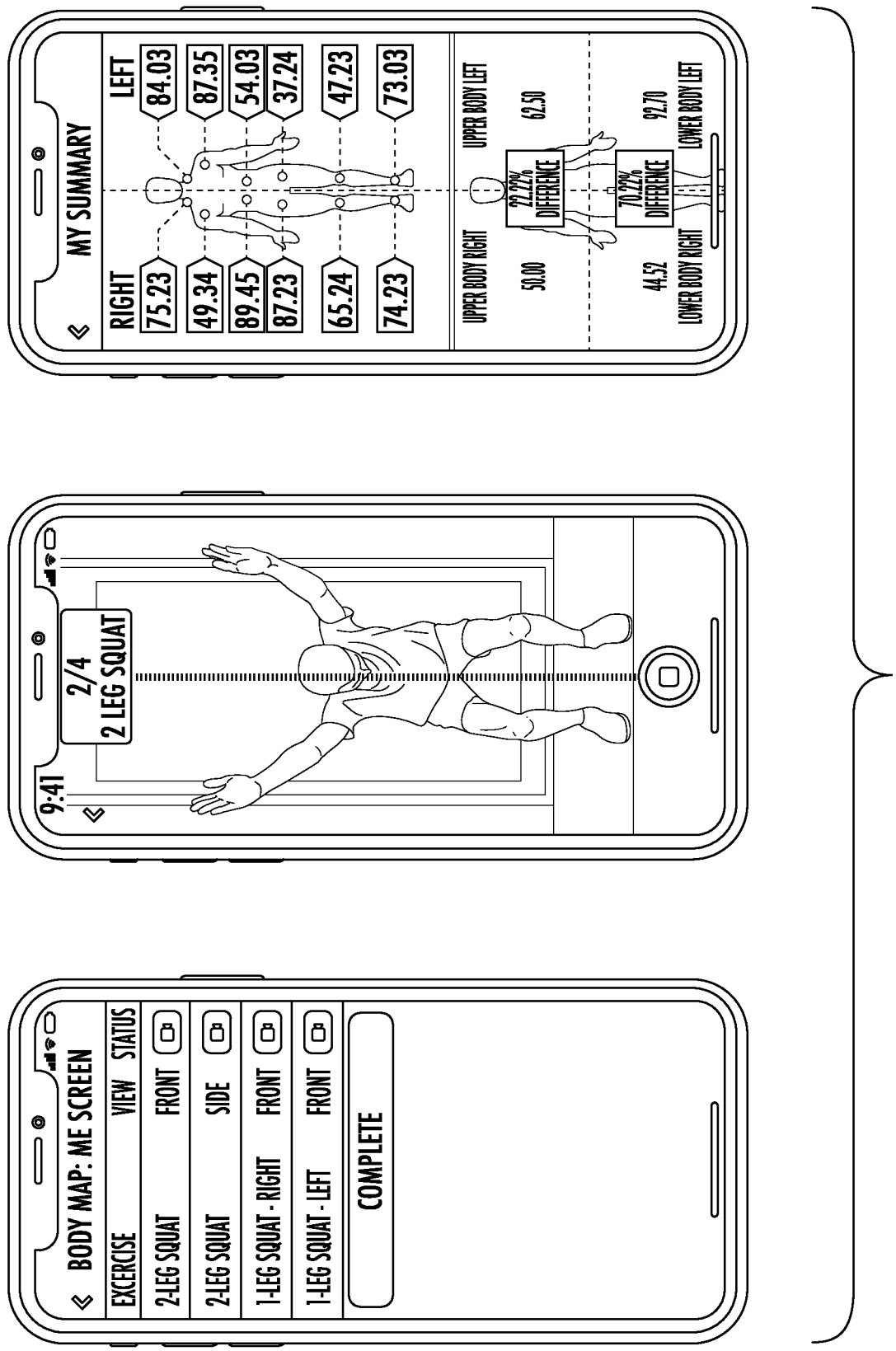

FIG. 6B illustrates a user interface which identifies user parameters determined during an initial assessment/baseline and/or subsequent exercises. The illustrated embodiment shows an exercise and relevant measured performance metrics (e.g., performance per muscle group, etc.)

Figure 6C:
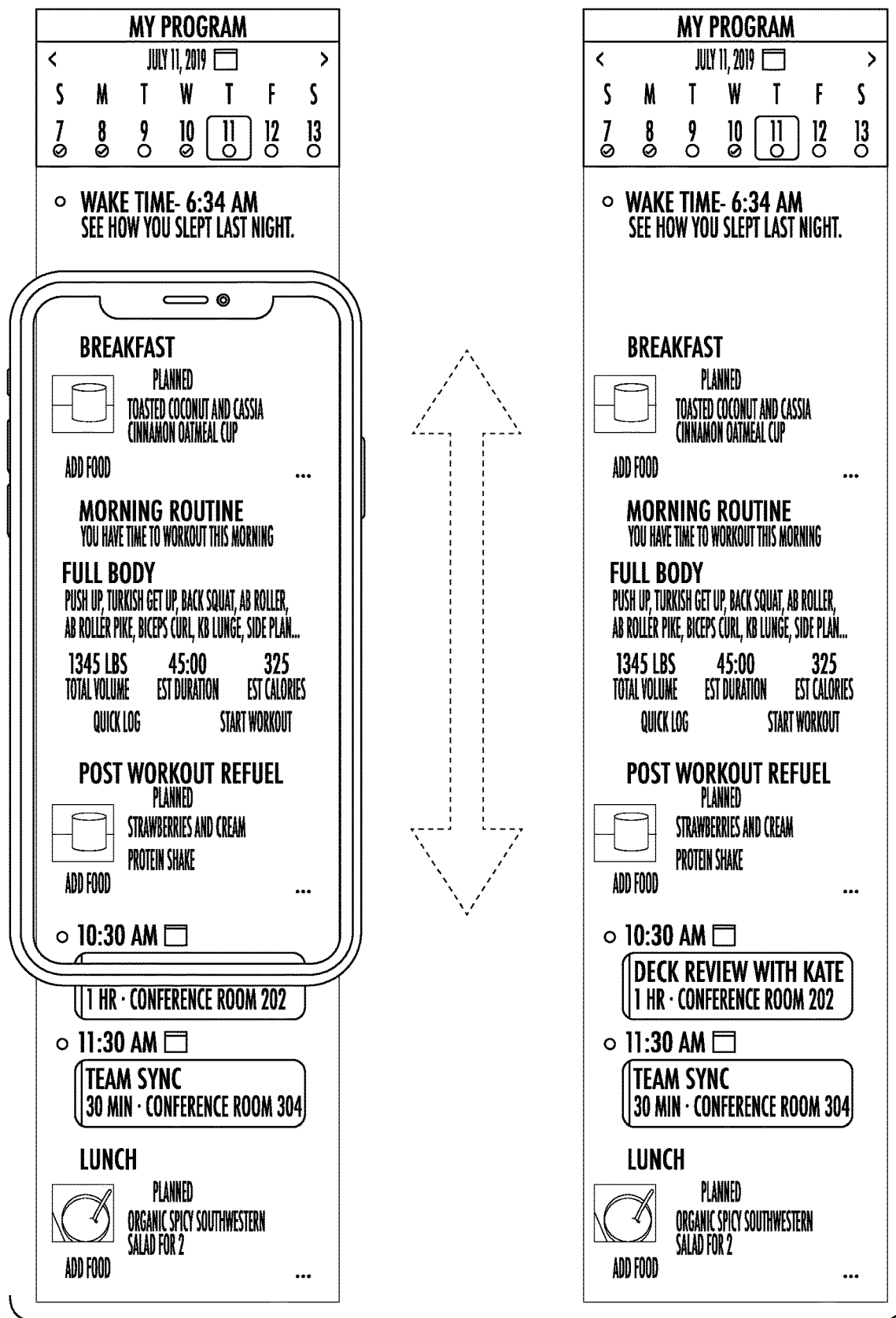

FIG. 6C illustrates a user interface which provides a program view that enables a user to manage their day-to-day personal fitness journey. In the illustrated embodiment, the program view provides a schedule of daily tasks to complete in order for users to stay on track, avoid injury, and succeed in their personal goals. The program view provides a complete training plan that incorporates workouts, nutrition, and sleep. In one exemplary embodiment, the program includes actionable steps (e.g., meals to eat, times to sleep, workouts to complete, etc.) that are automatically populated and/or manually re-configurable in view of the user's scheduling constraints (e.g., personal and professional appointments). The actionable steps are generated based on the expected profile that is associated with the user.

FIG. 6D illustrates a user interface which dynamically generates a workout based on e.g., physiological and/or psychological user input. Specifically, a workout is generated based on readiness inputs, current location, and workout schedule. The workout intensity may be modified based on readiness inputs and past rate of perceived effort (RPE) inputs. The workout length may be adjusted to complete before upcoming events in the user's calendar. Location information may be used to recommend exercises based on the available equipment at the workout location.

Figure 6E:
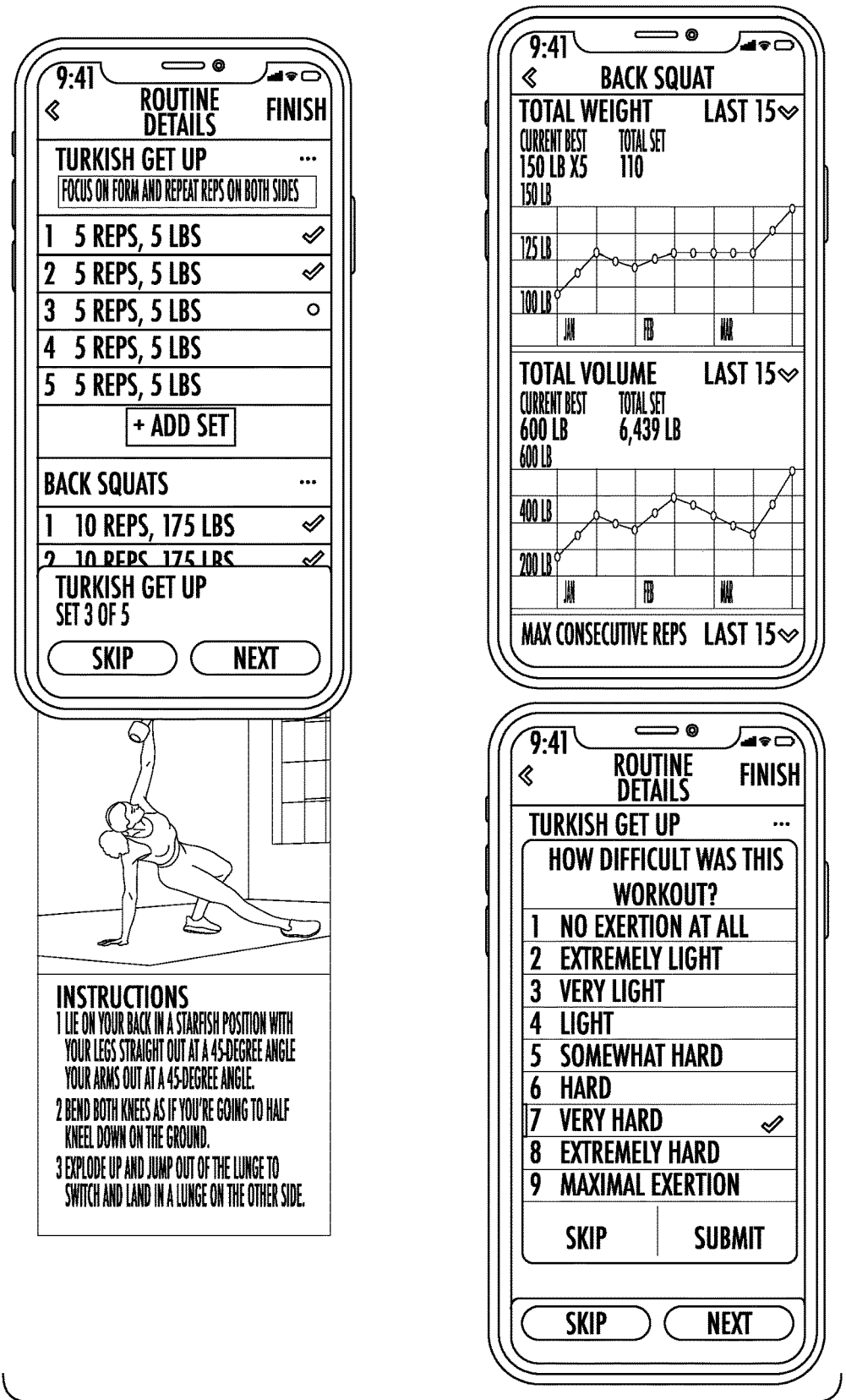

FIG. 6E illustrates a user interface which recommends and provides dynamic feedback to users during their workout regimen. The interface provides informative references for the exercise, and visual indication on routine progress. During the workout, the user is prompted to provide Rate of Perceived Effort (RPE) feedback along the way. RPE can be used to provide dynamic feedback as well as improve future workout recommendations.

Figure 6F:
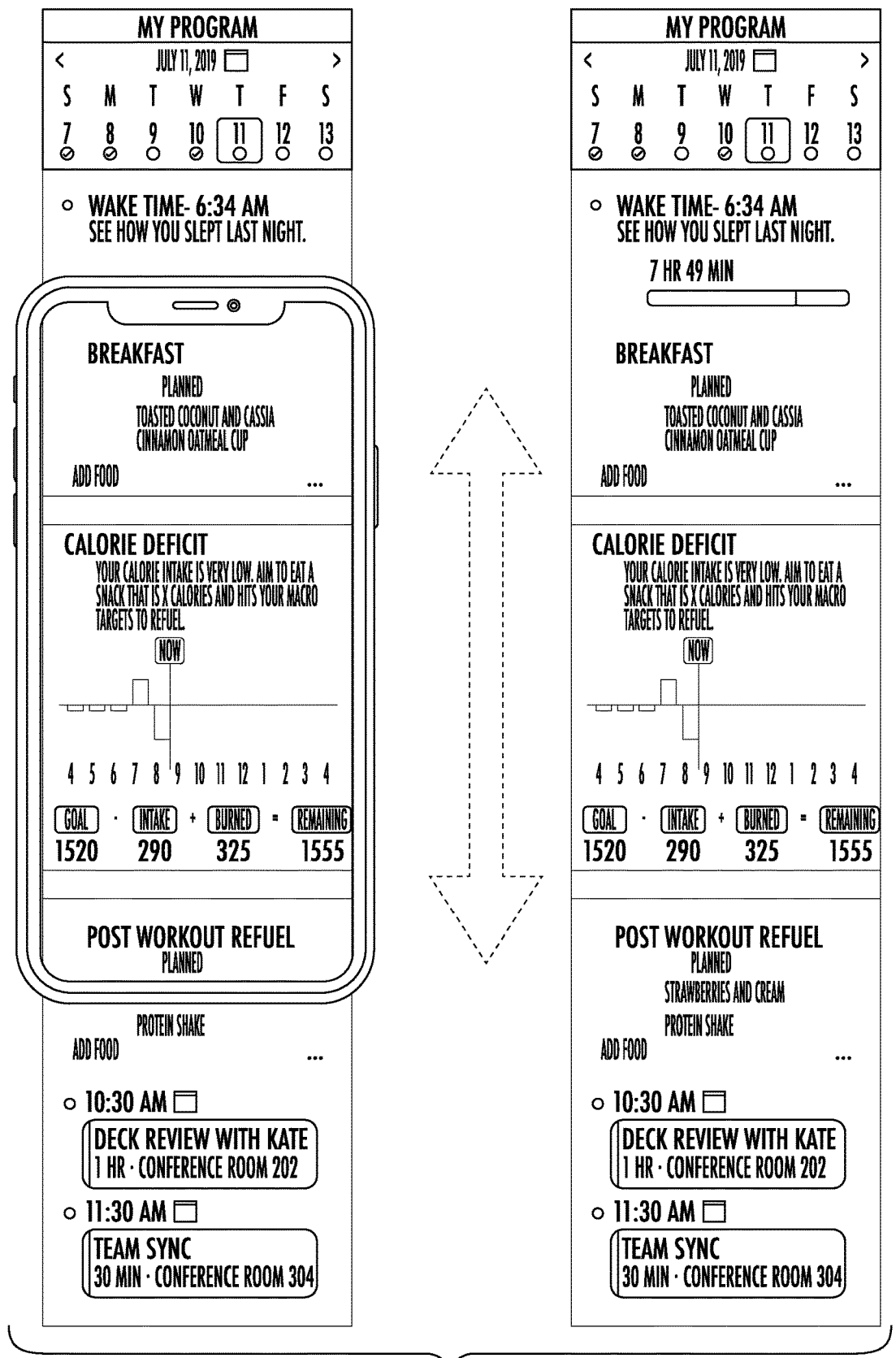

FIG. 6F illustrates updates to the aforementioned program view based on the user's activity. In the illustrated embodiment, the program view has updated the user's daily tasks with information regarding the user's actual behavior. For example, as shown in FIG. 6F, the user's sleep quality is provided (e.g., 7 hr 49 min) along with qualitative measurements that were gathered from the user's sleep tracking devices. Similarly, the user's workout activity is updated to reflect caloric and/or hydration deficits as a function of time; this data can be used for updating (increasing/decreasing if necessary) post-workout refuel snack/meal suggestions.

In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system with workout coaching has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

In another embodiment, a permanent copy of the programming instructions for individual ones of the aforementioned applications may be placed into permanent storage devices (such as e.g., memory) during manufacture thereof, or in the field, through e.g., a distribution medium (not shown), such as a compact disc (CD), or through communication interface (from a distribution server). That is, one or more distribution media having an implementation of the agent program may be employed to distribute the agent and program various computing devices.

It will be appreciated that the various ones of the foregoing aspects of the present disclosure, or any parts or functions thereof, may be implemented using hardware, software, firmware, tangible, and non-transitory computer-readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method for dynamically coaching a user based on one or more readiness metrics, comprising:
    obtaining the one or more readiness metrics from a first device of a user's personal community of devices;
    obtaining a recommended workout and a profile from a server, where the recommended workout comprises a plurality of exercises and the profile comprises a performance metric;
    adjusting the performance metric prior to the recommended workout based on the one or more readiness metrics;
    monitoring a performance during the recommended workout at a second device of the user's personal community of devices, the second device configured to collect physiological data; and
    when the performance does not match the adjusted performance metric, modifying at least one exercise of the recommended workout based on the profile.

2. The method of claim 1, wherein the one or more readiness metrics comprises an amount or quality of sleep measured by the first device.

3. The method of claim 1, wherein the one or more readiness metrics comprises an estimated caloric availability estimated by the first device.

4. The method of claim 1, wherein the one or more readiness metrics comprises a subjective input provided by the user via the first device.

5. The method of claim 1, further comprising adjusting the recommended workout based on a shortened available duration.

6. The method of claim 1, further comprising providing dynamic feedback based on the one or more readiness metrics.

7. The method of claim 1, further comprising causing a workout data record to be updated at the server based on the one or more readiness metrics.

8. A user apparatus, comprising:
    a sensor configured to collect physiological data;
    a user interface;
    a network interface configured to communicate with a community of user devices;
    a processor; and
    a non-transitory computer-readable medium comprising one or more instructions, which when executed by the processor, causes the user apparatus to:
    collect the physiological data via the sensor;
    generate a readiness metric based on the physiological data; and
    provide the readiness metric to a first device of the community of user devices prior to a scheduled recommended workout comprising a plurality of exercises;
    wherein the readiness metric causes the first device to adjust a performance metric prior to the scheduled recommended workout based on the readiness metric.

9. The user apparatus of claim 8, wherein the readiness metric comprises an amount or quality of sleep measured before the scheduled recommended workout.

10. The user apparatus of claim 8, wherein the readiness metric is based on a step count measured before the scheduled recommended workout.

11. The user apparatus of claim 8, wherein the readiness metric is estimated based on subjective user input.

12. The user apparatus of claim 8, wherein the user apparatus comprises a sleep tracking device and the first device of the community of user devices comprises a smart phone.

13. The user apparatus of claim 8, wherein the user apparatus comprises a smart watch and the first device of the community of user devices comprises a smart phone.

14. The user apparatus of claim 8, wherein the user apparatus comprises a smart shoe and the first device of the community of user devices comprises a smart phone.

15. A user apparatus, comprising:
    a sensor configured to collect physiological data;
    a user interface;
    a network interface configured to communicate with a community of user devices;
    a processor; and
    a non-transitory computer-readable medium comprising one or more instructions, which when executed by the processor, causes the user apparatus to:
    collect a readiness metric via the community of user devices;

obtain a recommended workout comprising a plurality of exercises and a profile comprising a performance metric;

adjust the performance metric prior to the recommended workout based on the readiness metric;

monitor performance during the recommended workout based on the physiological data; and modify at least one exercise of the recommended workout based on the profile and the readiness metric.

16. The user apparatus of claim 15, wherein at least one device of the community of user devices comprises a sleep tracking sensor;

wherein the readiness metric comprises an amount or quality of sleep measured before the recommended workout.

17. The user apparatus of claim 15, wherein the one or more instructions, when executed by the processor, further causes the user apparatus to:

log one or more consumption events; and estimate the readiness metric based on the one or more consumption events before the recommended workout.

18. The user apparatus of claim 15, wherein the one or more instructions, when executed by the processor, further causes the user apparatus to:

solicit subjective user input prior to the recommended workout; and estimate the readiness metric based on the subjective user input.

19. The user apparatus of claim 15, wherein at least one device of the community of user devices comprises a smart shoe;

wherein the readiness metric comprises a step count measured before the recommended workout.

20. The user apparatus of claim 15, wherein at least one device of the community of user devices comprises a smart watch;

wherein the readiness metric comprises a subjective user input obtained before the recommended workout.

* * * * *